(12) United States Patent
Agnello et al.

(10) Patent No.: US 12,232,964 B2
(45) Date of Patent: Feb. 25, 2025

(54) BIOABSORBABLE TEXTILES AND METHODS FOR JOINT FUNCTION RESTORATION

(71) Applicant: Anika Therapeutics S.r.l., Padua (IT)

(72) Inventors: Stefano Agnello, Grotte (IT); Edward Ahn, Dover, MA (US); Matteo Centola, Padua (IT); Steven W. Ek, Bolton, MA (US); Stephen J. Kennedy, Hudson, NH (US); Matthew M. Mannarino, Burlington, MA (US); Elvira Marchetto, Abano Terme (IT); Sonali Puri, Ashland, MA (US); Robert Richard, Wakefield, RI (US); Sara Simoncioni, Senigallia (IT)

(73) Assignee: Anika Therapeutics, Inc., Bedford, MA (US)

( * ) Notice: Subject to any disclaimer, the term of this patent is extended or adjusted under 35 U.S.C. 154(b) by 551 days.

(21) Appl. No.: 17/456,901

(22) Filed: Nov. 30, 2021

(65) Prior Publication Data
US 2022/0168105 A1    Jun. 2, 2022

Related U.S. Application Data

(60) Provisional application No. 63/120,232, filed on Dec. 2, 2020.

(51) Int. Cl.
*A61F 2/30* (2006.01)
*A61L 27/20* (2006.01)
(Continued)

(52) U.S. Cl.
CPC ............... *A61F 2/30* (2013.01); *A61L 27/20* (2013.01); *A61L 27/32* (2013.01); *A61L 27/58* (2013.01); *D02G 3/448* (2013.01); *D03D 1/00* (2013.01); *D03D 19/00* (2013.01); *A61F 2002/30062* (2013.01); *A61F 2210/0004* (2013.01);

(Continued)

(58) Field of Classification Search
CPC .................................. A61F 2/30; D03D 19/00
See application file for complete search history.

(56) References Cited

U.S. PATENT DOCUMENTS

2007/0110819 A1* 5/2007 Pastorello ............. A61L 27/425
424/549

OTHER PUBLICATIONS

Cristino et al., Analysis of Mesenchymal Stem Cells Grown on A Three-Dimensional HYAFF 11-Based Prototype Ligament Scaffold: Analysis of Mesenchymal Cells, Journal of Biomedical Materials Part A; vol. 73A, No. 3, pp. 275-283. (Year: 2005).*

(Continued)

*Primary Examiner* — Carlos A Azpuru
(74) *Attorney, Agent, or Firm* — Silvia Salvadori, P.C.; Silvia Salvadori

(57) ABSTRACT

A bioabsorbable textile for the restoration of the joint function whereas the joint is affected by partial thickness tears, small to medium full-thickness tears, large to massive full-thickness tears, acute and chronic/degenerative tears. The bioabsorbable textile may comprise polymeric yarns interconnected to form a weave or knitted configuration, wherein said bioabsorbable textile provides a combined mechanical and biological augmentation in the target joint tissue. The bioabsorbable textile may be implanted in combination with fixation tools during open, mini-open or arthroscopic repair/augmentation procedures of joint tissue tears.

7 Claims, 30 Drawing Sheets

(51) Int. Cl.
    *A61L 27/32*     (2006.01)
    *A61L 27/58*     (2006.01)
    *D02G 3/44*     (2006.01)
    *D03D 1/00*     (2006.01)
    *D03D 19/00*     (2006.01)

(52) U.S. Cl.
    CPC ...... *D10B 2331/04* (2013.01); *D10B 2401/12* (2013.01); *D10B 2509/00* (2013.01)

(56) References Cited

OTHER PUBLICATIONS

Barber F.A. et al., "Tendon augmentation grafts: biomechanical failure loads and failure patterns", Arthroscopy: The Journal of Arthroscopic and Related Surgery, vol. 22, No. 5 May 2006: pp. 534-538.

Burkhart S. et al., "Cyclic loading of anchor-based rotator cuff repairs: confirmation of the tension overload phenomenon and comparison of suture anchor fixation with transosseous fixation", Arthroscopy: The Journal of Arthroscopic and Related Surgery, vol. 13, No. 6 (Dec. 1997: pp. 720-724.

Caliari S.R. et al., "The development of collagen-GAG scaffold-membrane composites for tendon tissue engineering, " Biomaterials Dec. 2011: 32(34): 8990-8998.

Chen J et al., "Scaffolds for tendon and ligament repair: review of the efficacy of commercial products, " Expert Rev Med Devices 6(1), 61-73 (2009).

Coleman S. H et al., "Chronic rotator cuff injury and repair model in sheep", The Journal of Bone & Joint Surgery, vol. 85-A, No. 12, Dec. 2003.

Derwin K. A. et al., "Rotator cuff repair augmentation in a canine model with use of a woven poly-L-lactide device", J. Bone Joint Surg. Am. 2009;91:1159-71.

Funakoschi T et al., "Application of tissue engineering techniques for rotator cuff regeneration using a chitosan-based hyaluronan hybrid fiber scaffold", The American Journal of Sports Medicine, vol. 33, No. 8, 2005:1193-1201.

Grier W.K., et al., "The influence of pore size and stiffness on tenocyte bioactivity and transcriptomic stability in collagen-GAG scaffolds", J. Mech Behav Biomed Mater. Jan. 2017; 65:295-305.

Hughes R.E. et al., "Force analysis of rotator cuff muscles", Clinical Orthopaedics and Related Research, N. 330, pp. 75-83, 1996.

Kishore V. et al., "Tenogenic differentiations of human MSCs induced by the topography of electrochemically aligned collagen threads", Biomaterials Mar. 2012; 33(7):2137-2144.

Kraus V. B., et al., "Measurement of synovial fluid volume using urea", Osteoarthritis Cartilage Oct. 2007: 15 (10): 1217-1220.

Longo U.V., et al., "Tendon augmentation grafts: a systematic review", British Medical Bulletin 2010; 94:165-188.

Marques M.R.C. et al., "Simulated biological fluids with possible application in dissolution testing", Dissolution Technology, Aug. 31, 2011, pp. 15-28.

Minagawa H et al., "Prevalence of symptomatic and asymptomatic rotator cuff tears in the general population: from mass-screening in one village", Journal of Orthopaedics 10 (2013) 8-12.

Moffat K.L., et al., "Novel nanofiber-based scaffold for rotator cuff repair and augmentation", Tissue Engineering: Part A vol. 15, No. 1, 2009, 115-128.

Ratcliffe A. et al., "Scaffolds for tendon and ligament repair and regeneration", Ann Biomed Eng. Mar. 2015: 43 (3): 819-831.

Smith R. D.J. et al., "Characterizing the macro and micro mechanical properties of scaffolds for rotator cuff repair", J Shoulder Elbow Surg (2017) 2, 2038-2046.

Smith R.D.J. et al., "The response of tenocytes to commercial scaffolds used for rotator cuff repair", European Cells and Materials vol. 31 2016 (pp. 107-118).

Thangarajah T et al., "Augmentation of rotator cuff repair with soft tissue scaffolds", The Orthopaedic Journal of Sports Medicine, 3(6), 2015 1-8.

Tong W.Y. et al., "Functional replication of the tendon tissue microenvironment by a bioimprinted substrate and the support of tenocytic differentiation of mesenchymal stem cells", Biomaterials 33 (2012) 7686-7698.

Van Kampen C. et al., "Tissue-engineered augmentation of a rotator cuff tendon using a reconstituted collagen scaffold: a histological evaluation in sheep", Muscles, Ligaments and Tendons Journal 2013; 3(3):229-235.

Younesi M. et al., "Tenogenic induction of human MSCs by anisotropically aligned collagen biotextiles", Adv Funct mater. Sep. 24, 2014; 24(36): 5762-5770.

Zhang X. et al., "Biomimetic Scaffold Design for Functional and Integrative Tendon Repair", J. Shoulder Elbow Surg. Feb. 2012; 21(2): 266-277.

Cristino S. et al., "Analysis of mesenchymal stem cells grown on a three-dimensional HYAFF 11-based prototype ligament scaffold: Analysis of Mesenchymal Stem Cells", Journal of Biomedical Materials Research Part A, vol. 73A, 10. 3, Mar. 23, 2005, pp. 275-283.

Grigolo B, et al., "Osteoarthritis treated with mesenchymal stem cells on hyaluronan-based scaffold in rabbit", Tissue Engineering. Part C, Methods Dec. 2008, vol. 15, No. 4, Dec. 10, 2009, pp. 647-658.

Search Report and Written Opinion issued in connection of counterpart international application PCT/EP2021/083575 on Mar. 7, 2022.

\* cited by examiner

| | Max load (N) | St.Dev. | % of Max Load retained |
|---|---|---|---|
| Dry | 48.83 | 8.12 | |
| 1min | 22.55 | 1.82 | 46.18 |
| 5min | 19.08 | 1.44 | 39.06 |
| 10min | 19.80 | 1.66 | 40.55 |
| 1h | 19.67 | 2.26 | 40.29 |
| 5d | 19.80 | 0.57 | 40.55 |
| 12d | 17.69 | 1.44 | 36.23 |
| 20d | 14.43 | 0.83 | 29.55 |
| 28d | 17.15 | 1.09 | 35.12 |
| 42d | 14.85 | 1.44 | 30.42 |
| 152d | 11.97 | 0.76 | 24.51 |

BIOABSORBABLE TEXTILES AND METHODS FOR JOINT FUNCTION RESTORATION

This Non-Provisional application claims priority from and the benefit of the of U.S. Provisional Application No. 63/120,232 filed Dec. 2, 2020 the content of which is herein incorporated by reference in its entirety.

TECHNICAL FIELD OF INVENTION

The present invention relates to textiles for treatment of joint tears. More particularly, the invention relates to bioabsorbable compositions and surgical methods aimed at mechanically and biologically augmenting the repair of joint tears with the ultimate goal to minimize re-tear rates and to restore tissue function.

BACKGROUND OF INVENTION

Rotator cuff acts to stabilize the shoulder. Rotator cuff tears are a common source of debilitating pain, weakness and reduced shoulder function, which can lead to degenerative changes in the glenohumeral joint over time (Lehman, 1995). Rotator cuff tears affect up to 22% of the general population, with the incidence increasing as the population ages (Yamamoto, 2010; Minagawa, 2013). Full-thickness tears alone are estimated to have a prevalence of 28% for >60 years-old patients and 50% for >80 years-old patients (Tashjian, 2012).

The complex anatomy of the shoulder, the extended range of motion of this joint, as well as the hypovascularity of tendons and the relative weakening associated with tissue degeneration contribute to the impaired healing of these tears and impose significant challenges in the treatment of these disorders (Ratcliffe, 2015).

In some cases, partial- and full-thickness tears can be treated non-operatively with conservative therapies; however, the vast majority are treated operatively, by surgical repair involving sutures, anchors and staples.

Multiple studies have documented significant re-tear rates between 5% (Bishop, 2006) and 90% (Galatz, 2004) in arthroscopically-managed tears, with those of larger size being more at risk.

Generally, the defective healing of the damaged rotator cuff tendon(s) is the main reason for repair failure. Patients who re-tear have reduced functional outcome and fewer treatment options available, often involving the unwanted and unpleasant scenario of a second surgical intervention that is often the shoulder arthroplasty (Smith, 2016).

A method of improving the mechanical integrity of rotator cuff tendon repairs is the application of a reinforcement device or scaffold. Tendon repair can be mechanically-augmented using a device grafted to the lesion area and fixed to the native tissue(s) with additional sutures and anchors, overall indicated as an augmentation technique (Zhang, 2012).

Scaffolds can be broadly categorized into 3 different categories: biological, synthetic, and a combination thereof (biosynthetic).

Biological devices (allografts or xenografts) are typically derived from decellularized extracellular matrix (ECM) of human, porcine, bovine and equine origin. The most common tissue sources are small intestine submucosa (SIS), dermis and pericardium, which are processed through cascade steps, to remove any non-collagen components (Longo, 2010). Common disadvantages of this category are the possibility of immune reaction, including the potential for graft rejection, the persistence of chronic inflammation and the risk of disease transmission due to the presence of genetic or infectious material in their composition (Chen, 2009).

Moreover, there is a high product variability and the need for long preparation time (hydration protocol) before entering in the operating room, which is never a preferred option for the end-users. Furthermore, these biological devices inherently possess significant safety risks linked to possible residual xenogenic DNA and to a strong foreign body reaction following the implantation.

Considering the strong disadvantages associated to the biological devices, an increasing interest has been focused in the development and use of synthetic devices. However, these devices are also associated to some drawbacks, such as: (i) the slow degradation time (>2 years), eventually associated with long-term problems related to long-term fatigue of the materials, (ii) poor support for tissue ingrowth and new tissue formation, (iii) poor integration into native tissue, and (iv) persistent low-level inflammatory response.

Generally, the synthetic augmentation devices are optimized around one single feature that is intrinsically associated to the raw material comprising a given device. For example, X-Repair (Synthasome), a poly-L-lactide-based woven scaffold was specifically designed with mechanical properties that are the most similar to human tendon among the commercially available augmentation scaffolds; however it is not able to support an effective biological healing and may be associated with a high risk of long-term inflammation associated to the slow degradation time of polylactic acid (Derwin 2009).

Even though more than 20 devices have been commercially available for the past 3 decades, few have demonstrated clinical efficacy in the context of surgical rotator cuff repair (Smith, 2017) and none have been implemented into routine clinical practice (Thangarajah, 2015). The inadequacy of existing scaffolds is partly due to the fact that they have not been specifically designed for rotator cuff repair, but for other specific uses, such as for anterior cruciate ligament (ACL) replacement, diabetic wound or Achilles tendon repair, or for a broad range of surgical repair applications.

None of the commercially-available devices have demonstrated the ability to effectively restore the highly hierarchical histological architecture of the native tendon tissue (Tong, 2012; Kishore, 2012; Younesi, 2014).

In conclusion, none of the developed devices aimed at repairing, reinforcing and/or augmenting rotator cuff tendons achieve the desired outcomes and this explains the low adoption rate of the rotator cuff augmentation technique many years after the technique was invented. Therefore, the scientific and the orthopedic community still demands viable, durable and effective solutions to provide patients with a valid therapeutic option, which is not yet available in the market.

No commercially-available devices meet the requirements for functional joint tissue healing, and this explains the low adoption rate that the surgical techniques aimed at preserving and not replacing the joint tissue(s) have shown to date in clinical practice. Thus, the orthopedic and, more importantly, the patient community still demands viable, durable and effective therapeutic solutions, alternative to the more invasive total joint arthroplasties or autografts that become less and less favorable considering their irreversible shortcomings.

An ideal device for functional and integrative joint restoration must first meet the physiological demand of the native tissue by promoting host cell-mediated healing while also providing a mechanical augmentation. Furthermore, the device should be biodegradable in order to be gradually replaced by new tissue.

More specifically, a typical tensile stress/strain relation for tendon is showed in FIG. 1. The mechanical properties of an ideal rotator cuff augmentation device should be similar to those of tendon to minimize complications due to compliance mis-match.

The mechanical design inputs for such devices are (Funakoshi, 2005):

Strength greater than the peak in vivo loads experienced by the repair tissue and preferably similar to the tissue itself, therefore ensuring that the device will not fail under physiological loads (FIG. 1).

Stiffness that allows for substantial load sharing, providing reinforcement and at the same time ensuring some load will be applied across the repair site, required for optimal biologic repair (FIG. 1).

Strain within the toe region of a load-displacement curve rather than experiencing loads in the linear stiffness region (FIG. 1).

A device for tendon repair should reach a maximum load as high as possible in the range of 50-800 N and within a strain at ultimate tensile stress of 0.5-8%. Suture retention strength is an additional fundamental property for the device. The suture pull-out strength should be high enough to resist functional loading, moreover, the elongation required for this load should be very low.

Additional requirements for an ideal device aimed at restoring joint function are biocompatibility and tolerability of both the intact device and its degradation products, as well as ease of handling and fitting for possible arthroscopic application (Moffat, 2009).

On the other hand, the biological properties of a device for joint tissue restoration can be enhanced with surface properties biomimicking the native structure. Hence, biologically relevant design inputs include high surface area to volume ratio, low density, high porosity, variable pore size, pore morphology, fiber orientation and microscale mechanical properties approximating those of the native tendon tissue. All these structural characteristics have been shown to significantly influence cell behaviors such as adhesion, growth, and differentiation, and neo-tissue formation. For example, in vitro studies have revealed that scaffold topography and fiber orientation, roughly recapitulating the architecture of the collagen-rich joint tissue matrix, positively regulate cell response thereby improving likelihood for a successful joint tissue repair (Kishore, 2012). In particular, the alignment of scaffold fibers promoted cell orientation along the longitudinal axis of the fibers, mimicking the physiological mature tenocytes disposition in native tendon; the matrix stiffness instead was found to influence cell differentiation and new collagen deposition (Grier, 2017).

Lastly, the device must integrate with the host joint tissue as well as with all the other surrounding tissues in the joint (typically bone) by promoting the regeneration of the native tissue interface.

Only an unprecedented, non-obvious, tuned and integrated combination of the above-listed features will result in a clinically-effective solution for treating joint tears, ultimately offering to the surgeons and the patients a viable and long-lasting regenerative solution that preserves the shoulder joint and avoid or delay a total arthroplasty intervention.

A possible solution to the above-mentioned demands may be offered by the development and/or by the use of novel biocompatible and degradable biomaterials with mechanical and biological properties that are fine-tuned to match specific requirements (Funakoshi, 2005; Caliari, 2011).

The present invention aims at providing a device satisfying all the above listed needs, by also overcoming the disadvantages of the prior art devices.

SUMMARY OF THE INVENTION

Therefore the present invention relates to a bioabsorbable textile for joint function restoration, wherein the bioabsorbable textile comprises polymeric yarns, wherein said bioabsorbable textile provides a combined mechanical and biological augmentation in the target joint tissue, and wherein at least one of said polymeric yarns comprises a hyaluronic acid derivative.

In the preferred embodiment said hyaluronic acid derivative is an ester, more preferably a benzyl ester. When compared to all the other solutions so far proposed to solve the problem, the present invention is the only one able to lead to a functional joint tissue restoration due to the combination of all the ideal features a soft tissue healing requires, such as (i) augmenting the mechanical properties to immediately match the behavior of the native joint tissue, (ii) simultaneously promoting host cell-mediated healing by mimicking the peculiar ultrastructural organization of the native joint tissues (iii) slowly resorbing to allow gradual replacement by new tissue, and (iv) finally integrating with the host joint tissue by promoting the regeneration of the native tissue.

The present invention was made possible by the unexpected and surprising finding that it is possible to create mechanically-robust, bioabsorbable textiles from hyaluronic acid (HA) derivatives, thereby leveraging their unique properties that make them perfectly suitable for the target application—i.e. restoring joint tissue function.

HA derivatives and their advantages, with a particular relevance for benzyl esters of HA and more in particular for full benzyl esters of HA have already been described elsewhere (U.S. Pat. No. 4,965,353, WO93/11805, WO94/03212, U.S. Pat. No. 6,482,231, WO99/61080 and WO99/65534). For the purpose of this invention, it is important to note how HA needs to be derivatized in a hydrophobic form to make it workable as a solid with a plurality of technologies, such as spinning, weaving, knitting, embroidery, etc.

The present invention is capable to meet all the above-mentioned design inputs so representing an innovative solution to effectively treat joint tissue tears.

The applicant has unexpectedly found a tailored combination of device design and raw material that are capable to provide (i) an immediate augmentation of the mechanical reinforcement of the lesion site, (ii) a temporary structure mimicking the native architecture of the target joint tissues, (iii) a sustained pro-regenerative environment during the joint tissue healing, and (iv) an in vivo degradation matching the new tissue formation.

Therefore the present invention relates a bioabsorbable textile for joint function restoration, wherein the bioabsorbable textile comprises polymeric yarns, wherein said bioabsorbable textile provides a combined mechanical and biological augmentation in the target joint tissue, and wherein at least one of said polymeric yarns comprises a hyaluronic acid derivative.

In the preferred embodiment said hyaluronic acid derivative is an ester, more preferably a benzyl ester. In another aspect the invention relates to the bioabsorbable textile of the invention for use in restoring joint function affected by partial thickness tears, small to medium full-thickness tears, large to massive full-thickness tears, acute and chronic/degenerative tears.

In a still another aspect the invention relates to the bioabsorbable textile of the invention for use in surgery in combination with fixation tools during open, mini-open or arthroscopic repair/augmentation procedures of joint tissue tears.

Without being bound to any theory the inventors deem that the present textile allows a biological and mechanical augmentation in the joint target tissue due not only to its polymeric nature but also to the configuration designs as it will be evident from the experimental part.

In an advantageous embodiment the preferred leno-weave or knitted configurations combined together with the use of a hyaluronic acid derivative, preferably benzyl ester of hyaluronic acid, make the bioabsorbable textile especially suitable for mechanical augmentation of the target joint.

The textile of the invention could be also considered as a new biomaterial in view of its mechanical and biological properties conferred to the target joint.

In a further aspect the invention relates to a multilayer structure for joint function restoration comprising at least one bioabsorbable textile according to the invention.

It is known that an appropriate mechanical reinforcement of the lesion site not coupled with a proper device degradation may result either in long-term safety issues, should the device be present in vivo too long (e.g. >6 months) or in implant failure (re-tear), should the device be present in vivo too short (e.g. <1 month). It is known that an appropriate mechanical reinforcement of the lesion site not coupled with a remodeled and mature tissue formation may result in the formation of sub-optimal fibrotic tissue that will ultimately lead to the implant failure (re-tear).

On the other hand, it is known that a sustained tissue regeneration not coupled with a matching device degradation may result either in long-term safety issues and/or in histologically-unacceptable outcome, should the device be present in vivo too long (e.g. >6 months) or in implant failure (re-tear), should the device be present in vivo too short (e.g. <1 month).

It appears evident how the only, though not obvious, solution associated with the highest chance to succeed clinically would be provided by a novel device capable to offer all these features at the same time.

The invention will be now detailed with reference to also the following figures.

BRIEF DESCRIPTION OF THE DRAWINGS

FIG. 15 shows the results of the preliminary evaluation of the efficacy and local tissue response in a sheep model, specifically an intraoperative picture of FIG. 15A) bioabsorbable textile implanted;

DETAILED DESCRIPTION OF THE INVENTION

Figure 1:
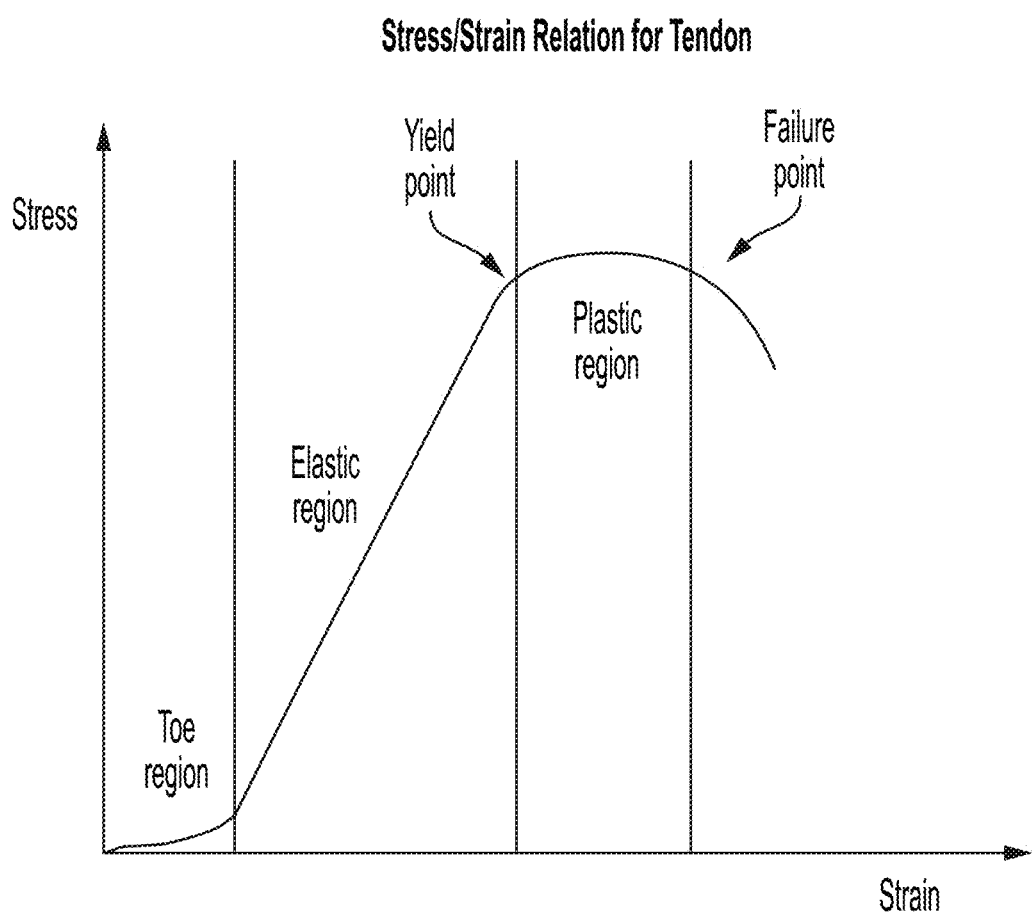
FIG. 1 shows a typical tensile stress/strain relation for tendon/ligament.

The present invention is directed to a bioabsorbable textile that provides a combined mechanical and biological augmentation at the lesion site aimed at favoring the formation of a mature, hierarchically-organized joint tissue.

In another aspect the invention relates to a device comprising the bioabsorbable textile of the invention. The degradation kinetics of the bioabsorbable textile will match the de novo tissue formation timelines so that the textile will only be present in situ for the time where this augmentation is really needed, ultimately maximizing the efficacy of the treatment as well as the safety profile of the textile.

The present invention provides a novel treatment option for patients suffering with joint pain and lack of joint function restoration in the knee, hip, shoulder, ankle, fingers, toes, wrist, elbow and vertebrae. Preferred embodiments of the inventive treatment augment the rotator cuff tendons via mechanical reinforcement and induction of tissue regeneration by reinforcing the suture- and/or anchor-based surgical rotator cuff repair in order to prevent further re-tears and alleviate the corresponding pain in the joint.

The bioabsorbable textiles can be prepared starting from the extrusion of the yarn using any technique familiar to those skilled in the art selected from the group consisting of melt spinning, ring spinning, air-jet spinning, open-end spinning, mule spinning, wet spinning, dry spinning, electrospinning, or extrusion. In a preferred embodiment, yarn composing the bioabsorbable textiles is extruded using a wet spinning technique.

In a preferred embodiment, yarn composing the bioabsorbable textile may be obtained starting by the dissolution of polymeric material powder in dimethyl sulfoxide (DMSO) at a concentration ranging from about 130 mg/ml to about 160 mg/ml prepared in a chemical reactor at a temperature of about 30° C. in order to obtain a viscosity ranging from about 70 to about 85 Pa*s. This dissolution is performed in two subsequent steps, namely about 75% of the DMSO calculated to obtain the target concentration and viscosity is initially used and mixed for about 60 minutes using a mixing speed ranging from about 50 to about 60 rpm. Afterwards, the remaining 25% of DMSO is added to the solution and mixed for a minimum of 3 hours at about 60 rpm and then overnight at about 20 to 30 rpm. Once the dissolution phase is completed, the polymeric solution is filtered for about 2 to about 3 hours using a nitrogen pressure of about 30 psi and a temperature of about 86° F. After the filtration phase, the polymeric solution is then degassed for about 18 hours using a degas pressure ranging from about 20 to 30 inHg and a temperature of about 86° F. The polymeric solution is then fed by a peristaltic pump at a speed of about 1.6 rpm into a spinneret for wet spinning composed of 150 holes each measuring 65 microns in diameter. The extruded multi-filament yarn is passed into a coagulation bath containing special denatured alcohol (SDA) comprising 80% absolute ethanol and 20% acetone and is then moved over transporting rollers into three successive rinsing baths, also containing SDA. The speeds of the single rollers are set at about 3.8 rpm. Once the multi-filament yarn has been passed through the rinsing baths, it is dried with warm air at a temperature ranging from about of 25° C. to about 45° C. and collected onto rotating cylindrical bobbin cores mounted onto a winding frame. These bobbin cores are switched every 2 to 3 hours.

In some embodiments, the multifilament yarn comprising the bioabsorbable textile may comprise a plurality of polymeric materials selected from the group consisting in polyethers, polyesters, polyols, poloxamers, proteins, polysaccharides (e.g. HA and its derivatives) or a combination thereof. In some embodiments, the extruded yarn will be lubricated by using a spin finish to allow downstream processability. In a preferred embodiment, the addition of a spin finish oil is applied at the end of the extrusion phase and, preferably, before any other manufacturing steps. Spin finish oils can have an origin selected from the group consisting of mineral oils, polymeric oils, or a combination thereof. In some embodiments, the spin finish content ranges between 0.1 mg per meter of yarn and 20 mg per meter of yarn. In a preferred embodiment, the spin finish content ranges between 1 mg per meter of yarn and 5 mg per meter of yarn.

The extruded yarn comprising the bioabsorbable textiles can be composed of mono- or multi-filaments. In some embodiments, yarns are composed of multi-filaments ranging from about 50 to about 10.000. In preferred embodiments, the number of filaments composing a single multi-filament yarn range from about 100 to about 150. In other preferred embodiments, the number of filaments composing a single multi-filament yarn range from about 5.000 to about 7.000.

In some embodiments, each filament composing a single multi-filament yarn has a mean diameter ranging from about 1 μm to about 100 μm. In preferred embodiments, the mean diameter of a single filament composing a single multi-filament yarn range from about 10 μm to about 40 μm. In a preferred embodiment, these filaments comprising the multi-filament yarn are separated to each other. In some embodiments, the extruded yarn comprising the bioabsorbable textile can display a diameter ranging from about 100 μm to about 3000 μm. In a preferred embodiment, the extruded yarn comprising the bioabsorbable textile can display a diameter ranging from about 200 to about 800 μm. In some embodiments, the extruded yarn comprising the bioabsorbable textiles can display a wet linear mass density ranging from about 10 tex to about 1.500 tex (where tex is a direct measure of linear density—i.e., number of grams per one kilometer of yarn). In a preferred embodiment, the extruded yarn displays a linear mass density ranging from about 30 tex to about 100 tex. In other preferred embodiments, the extruded yarn displays a linear mass density ranging from about 1.000 tex to about 1.300 tex.

In some embodiments, the extruded yarn comprising the bioabsorbable textiles can display a breaking strength ranging from about 1 N to about 100 N and an extension at break from about 1% to about 30%. In a preferred embodiment, extruded yarn displays a breaking strength ranging from about 4 N to about 12 N and an extension at break from about 1% to about 12%.

In a preferred embodiment the bioabsorbable textile according to the invention comprises the at least polymeric yarn which shows:
Linear mass density from about 30 tex to about 100 tex;
a breaking strength in the range from about 1 N to about 100 N, preferably from about 4N to about 12N, and
an extension at break from about 1% to about 30%, preferably from about 1% to about 12%.

In some embodiments, the extruded yarn comprising the bioabsorbable textiles can be twisted. In some embodiments, a yarn is produced by co-twisting together from one to about sixteen yarns in the opposite direction to make a thicker yarn. In a preferred embodiment, a yarn is produced by twisting one single yarn.

In some embodiments, the twisted yarn can have a number of twists per meter ranging from about 10 to about 1.000. In a preferred embodiment, the twisted yarn can have a number of twists per meter ranging from about 50 to about 500.

In some embodiments, the twisted yarn can have S twists (up-left direction) and in some other embodiments, the twisted yarn can have Z twists (up-right direction).

The bioabsorbable textiles can be prepared by interconnecting the extruded, and preferentially twisted yarn, using any technique familiar to those skilled in the art selected from the group consisting of weaving, leno weaving, knitting, spacer knitting fabric, braiding, crocheting, embroidery, ropemaking, and sewing.

In a preferred embodiment, the bioabsorbable textiles are prepared by weaving or leno weaving or by weft knitting or warp knitting. The bioabsorbable textile could be a weave where the ends of transversal (weft) direction yarns are structurally locked while the ends of longitudinal (warp) direction yarns remain open or a knitted structure.

The bioabsorbable textile could be a leno-weave in which a multiple amount of warp yarns is twisted around a single amount the weft yarns. In preferred embodiments, the leno-weave is composed by two to six warp yarns twisted around one to about two weft yarns.

In some embodiments, the bioabsorbable textiles are isotropic being woven with the same amount of yarns spanning along the longitudinal (warp) direction and the lateral (weft) direction. In a preferred embodiment, the bioabsorbable textiles are anisotropic with the amount of yarns in the warp direction being higher than the amount of yarns in the weft direction, where the warp direction corresponds to the direction of the tensile load in the target joint tissue. In a more preferred embodiment, the number of warp yarns per textile width ranges from about 10 yarns/cm to about 50 yarns/cm and the number of weft yarns per textile length ranges from about 4 yarns/cm to about 18 yarns/cm.

In preferred embodiments, the warp yarns are equally outdistanced throughout the textile width with the pore width (i.e. the distance between two adjacent warp yarns) ranging from about 1 to about 100 μm.

Figure 2A:
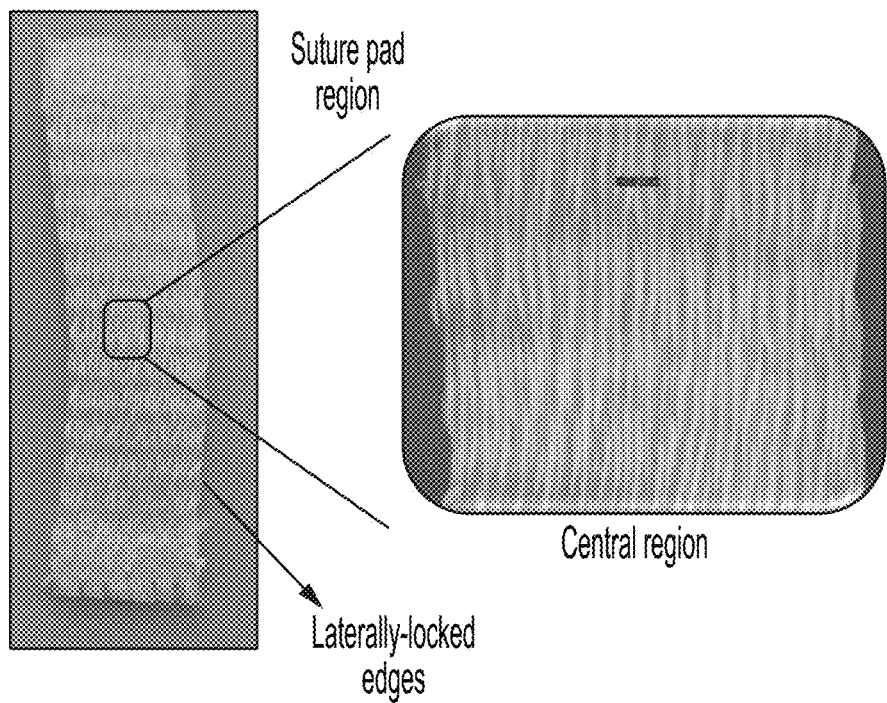
FIG. 2A shows an embodiment of the bioabsorbable textile of the invention (leno-woven bioabsorbable textile), wherein the weft yarns equally outdistanced throughout the textile length with the pore length.
Figure 2B:
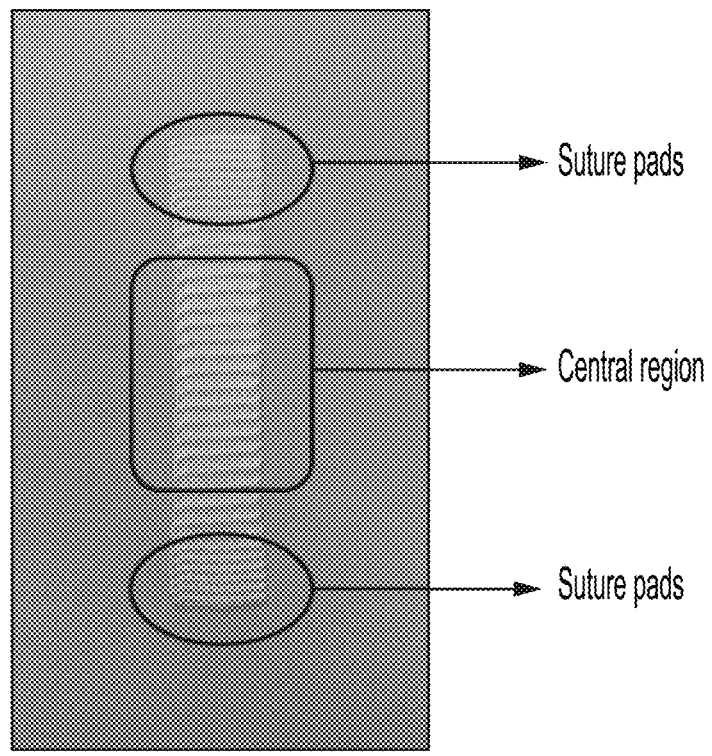
FIG. 2B shows another embodiment of the bioabsorbable textile of the invention (leno-woven bioabsorbable textile), wherein the weft yarns are equally distanced in the central region of the bioabsorbable textile.
Figure 2C:
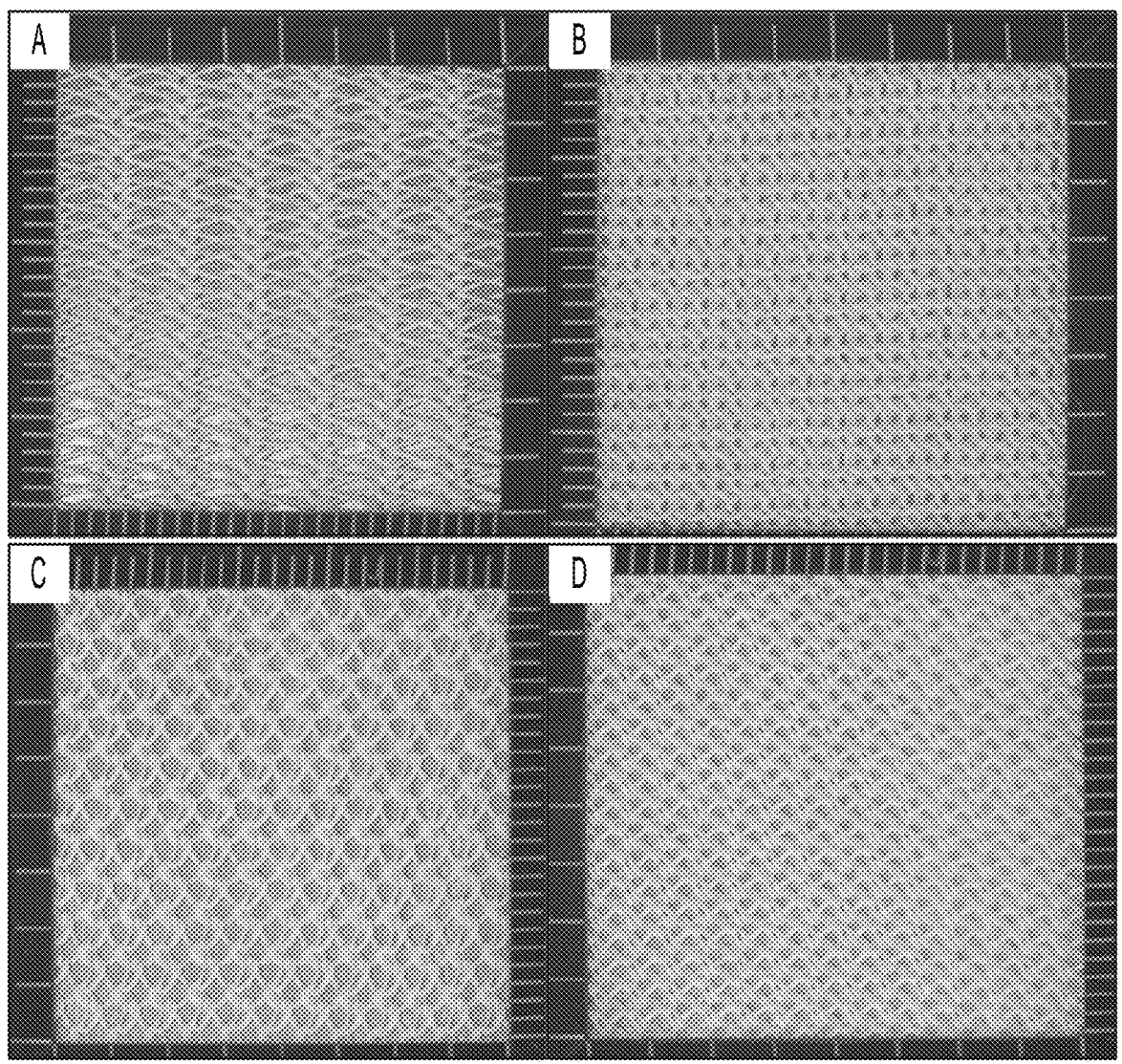
FIG. 2C contains four schematic representations of embodiments of the textile of the of warp-knitted bioabsorbable textile
Figure 2D:
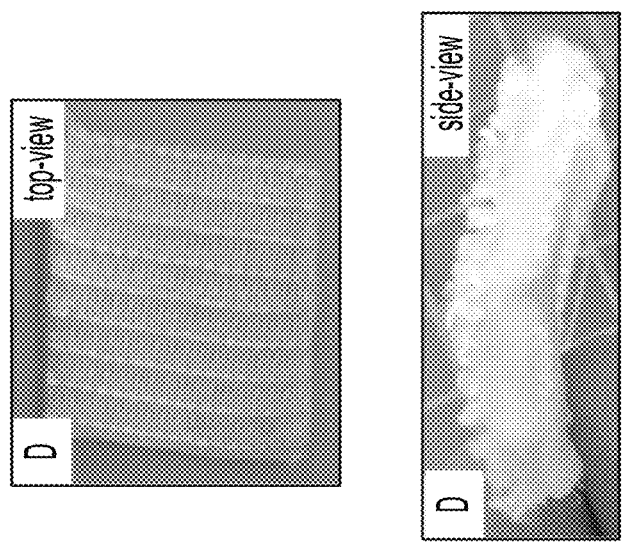
FIG. 2D is a schematic representation of preferred embodiments of the bioabsorbable textiles with single or a plurality of layers superimposed on each other, where each layer comprises textiles as described in FIG. 2A and in FIG. 2B) or nonwoven pad.
Figure 2D:
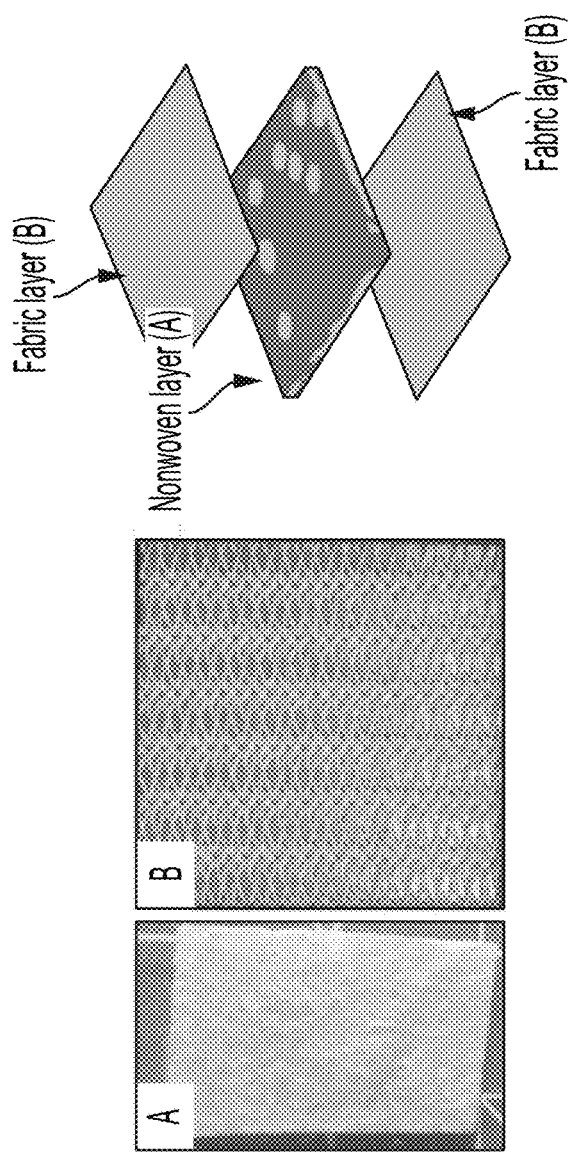

In some preferred embodiments, the weft yarns are equally outdistanced throughout the textile length with the pore length (i.e. the distance between two adjacent weft yarns) ranging from about 100 to about 2500 μm (FIG. 2A). In some other preferred embodiments, the weft yarns are equally distanced in the central region of the bioabsorbable textile, whereas the central region represents about 50 percent to about 80 percent with respect to the total textile length (FIG. 2B, Central region). In these preferred embodiments, the weft yarns are equally distanced within the central region of the textile with a pore length (i.e. the distance between two adjacent weft yarns within the central region of the textile) ranging from about 1300 μm to about 2300 μm. In these preferred embodiments, the number of weft yarns per textile length ranges from about 4 yarns/cm to about 10 yarns/cm.

In these preferred embodiments, the weft yarns are more densely packed at the external portions (top and bottom ends with respect to the central region) of the bioabsorbable textile in comparison with the central region of the textile, whereas the external portions represent about 25 percent to about 10 percent each with respect to the total textile length (FIG. 2B, Suture pads). In these preferred embodiments, the weft yarns are equally distanced within the external portions of the textile with a pore length (i.e. the distance between two adjacent weft yarns within the external portions of the textile) ranging from about 200 μm to about 700 μm. In these preferred embodiments, the number of weft yarns per textile length ranges from about 6 yarns/cm to about 18 yarns/cm.

As shown in FIG. 2, the denser, external regions are also referred as suture pads since their scope within the bioabsorbable textiles is to provide a reinforced area for suturing the textile to the target joint tissue to reduce the likelihood of sutures tearing the textile when strain is applied. The open ends of the warp yarns at the suture pads can be locked using any edge bonding technique familiar to those skilled in the art selected from the group consisting of solvent welding, embroidery, sewing, radiofrequency welding, ultrasonic welding, laser welding, and hot temperature welding. In some preferred embodiments, the top and bottom edges of the bioabsorbable textile are solvent-welded by laying down a thin layer of polymeric solution at the edges (FIG. 2B). In some other preferred embodiments, the top and bottom edges of the bioabsorbable textile are mechanically sealed via embroidery or sewing, where the initial reinforcement created by inserting straight stitches in a plurality of sets of a plurality of rows each (FIG. 2A). In preferred embodiments the reinforcement stitches are inserted as 2 sets of 3 rows each. In these preferred embodiments, reinforcement stitches are grouped by the addition of an overstitched stitch row. In some preferred embodiments, the overstitched stitch row displays a zig-zag pattern. In some embodiments, the reinforcement stitches and the overstitched stitch row comprising the suture pads of the bioabsorbable textile may comprise a plurality of polymeric materials selected from the group consisting in polyethers, polyesters, polyols, poloxamers, proteins, polysaccharides (e.g. HA and its derivatives) or a combination thereof. In a preferred embodiment, the reinforcement stitches and the overstitched stitch row comprising the suture pads of the bioabsorbable textile comprises a benzyl ester of hyaluronic acid modified with an esterification degree ranging from about 80% to about 100%. In some embodiments, the suture pads are folded on themselves and this step is followed by edge bonding. In preferred embodiments, the suture pads are suture-closed as a single, unfolded layer.

The bioabsorbable textile could be a knitted structure. 4 different design variants (FIG. 2C) were conceived by varying knit structure and two input parameters, namely the mesh areal density and the inter-yarn porosity.

In some embodiments, the bioabsorbable textiles may comprise single or a plurality of layers superimposed on each other, where each layer comprises textiles manufactured as described above or nonwoven pad (FIG. 2D).

In some embodiments, the bioabsorbable textiles may show a length ranging from about 5 mm to about 150 mm, a width ranging from about 5 to about 150 mm, and a thickness ranging from about 0.1 mm to about 5 mm. In a preferred embodiment, the bioabsorbable textiles may show a length ranging from about 15 mm to about 105 mm, a width ranging from about 5 to about 55 mm, and a thickness ranging from about 0.3 mm to about 3 mm.

Noteworthy, the above-mentioned values refer to the dry state of the bioabsorbable textiles. When hydrated in physiological conditions (i.e. pH of about 7.4 and temperature of about 37° C.), in some embodiments the bioabsorbable textiles, show a volumetric as well as a thickness swelling ratio ranging from about 0.1% to about 20%. In a preferred embodiment, the bioabsorbable textiles, may have a volumetric as well as thickness swelling ratio ranging from about 0.1% to about 5%.

When hydrated in physiological conditions (i.e. pH of about 7.4 and temperature of about 37° C.), in some embodiments the bioabsorbable textiles, show a weight swelling ratio ranging from about 0.1% to about 150%. In a preferred embodiment, the bioabsorbable textiles, may have a volumetric as well as thickness swelling ratio ranging from about 35% to about 80%.

Related to the above-mentioned physical sizes in dry conditions, in a preferred embodiment of the bioabsorbable textiles the areal density ranges from about 100 g/m$^2$ to about 1000 g/m$^2$. In preferred embodiments, the bioabsorbable textiles showed an accessible porosity ranging from about 20% to about 85%.

The bioabsorbable textiles can be prepared using yarns comprising a raw material selected from the group consisting in polyethers, polyesters (e.g. poly lactic acid, poly caprolactone, etc.), polyols (e.g., polyvinyl alcohol, polyethylene glycol, polypropylene glycol), poloxamers, proteins or natural polymers (e.g. chitosan, collagen, gelatin, alginate, etc.), polysaccharides (e.g. hyaluronic acid and its derivatives), or a combination thereof. In some embodiments, the bioabsorbable textile can be prepared using multiple yarns comprising different raw materials selected from the group consisting in polyethers, polyesters, polyols, poloxamers, proteins, polysaccharides (e.g. hyaluronic acid and its derivatives) or a combination thereof. In some other embodiments, the yarn comprising the bioabsorbable textile can consist of multi-filaments comprising one or multiple raw materials. In a preferred embodiment, the bioabsorbable textile can be prepared using yarns comprising only one raw material for each filament comprising the multi-filament yarn.

In preferred embodiments, the bioabsorbable textiles are prepared using multi-filament yarns comprising hyaluronic acid derivatives as raw material selected from the group consisting of hyaluronic acid esters wherein a part or all of the carboxy functions are esterified with alcohols of the aliphatic, aromatic, arylaliphatic, cycloaliphatic, heterocyclic series, especially with benzyl alcohol; cross-linked esters of hyaluronic acid wherein part or all of the carboxy groups are esterified with the alcoholic functions of the same polysaccharide chain or of other chains; cross-linked compounds of hyaluronic acid wherein part or all of the carboxy groups are esterified with polyalcohols of the aliphatic, aromatic, arylaliphatic, cycloaliphatic, heterocyclic series, generating cross-linking by means of spacer chains; hemiesters of succinic acid or heavy metal salts of the hemiester of succinic acid with hyaluronic acid or with partial or total esters of hyaluronic acid; 0-sulphated derivatives or N-sulphated derivatives; quaternary ammonium salts, such as salts with tetrabutylammonium and phenyltrimethylammonium, of hyaluronic acid or a hyaluronic acid derivative selected from the group consisting of N-sulphated hyaluronic acid, 0-sulphated hyaluronic acid, the hemiesters of succinic acid with hyaluronic acid and optionally partially salified with heavy metals. In more preferred embodiments, the bioabsorbable textiles are prepared using multi-filament yarns comprising benzyl esters of hyaluronic acid. In the most preferred embodiment, the bioabsorbable textiles are prepared using multi-filament yarns comprising a benzyl ester of hyaluronic acid modified with an esterification degree ranging from about 80% to about 100%.

The inventors found that, in order to favor and accelerate osteointegration, in some embodiments the bioabsorbable textile can be optionally coated by using any technique familiar to those skilled in the art selected from the group consisting of vapor deposition, chemical and electrochemical techniques, spraying, roll-to-roll coating, physical coating, or a combination thereof. In preferred embodiments, the bioabsorbable textile is coated by plasma spraying. In some embodiments, the coating material is an osteo-inductive and/or osteo-conductive material selected from the group consisting of hydroxyapatite, calcium phosphates, bone cements, demineralized bone matrix, titanium, magnesium, strontium, bioglasses, other resorbable glasses, or a combination thereof.

In another aspect the invention hence relates to a bioabsorbable textile coated with an osteo-inductive and/or osteo-conductive material selected from the group consisting of hydroxyapatite, calcium phosphates, bone cements, demineralized bone matrix, titanium, magnesium, strontium, bioglasses, other resorbable glasses, and a combination thereof.

In some embodiments, the coating is uniformly applied onto the whole textile surface. In preferred embodiments, the coating is applied only at one side of the textile that will be the side in direct contact with the bone or with the tendon-to-bone interface. In some embodiments, the coating thickness may range between 1 nm to 100 μm. Always in order to favor and accelerate osteointegration, in some other embodiments the bioabsorbable textile may be applied in combination with an injectable bone cement formulation. In preferred embodiments, the injectable bone formulation is applied onto either the tendon-to-bone interface or onto the textile implanted at the interface or in-between the interface and the textile. In some embodiments, the injectable bone formulation is applied before the textile is implanted; in some other embodiments, the injectable bone formulation is applied after the textile is implanted. In preferred embodiments, the injectable bone formulation comprises a solid phase comprising a material selected from the calcium phosphate cement family known to those skilled in the art. In preferred embodiments, the injectable bone formulation comprises a liquid phase comprising hyaluronic acid or its derivatives.

The Applicant have unexpectedly and surprisingly found that, in order to favor and accelerate tissue regeneration and healing, in some embodiments before implantation the bioabsorbable textile can optionally be mixed directly in the operating room with a biological component familiar to those skilled in the art selected from the group consisting of bone marrow aspirate, bone marrow aspirate concentrate, mesenchymal stem cells, bone marrow stem cells, adipose-derived stem cells, amniotic cells, micronized amniotic membrane, partially- or fully-digested tissue biopsies, aspirated adipose tissue, platelet rich plasma, autologous conditioned plasma, growth factors, or a combination thereof. In another aspect the invention hence relates to a bioabsorbable textile added with a biological component selected from the group consisting of bone marrow aspirate, bone marrow aspirate concentrate, mesenchymal stem cells, bone marrow stem cells, adipose-derived stem cells, amniotic cells, micronized amniotic membrane, partially- or fully-digested tissue biopsies, aspirated adipose tissue, platelet rich plasma, autologous conditioned plasma, growth factors, and a combination thereof. The Applicant also found that the combination of a given textile design with a given raw material in some embodiments, unexpectedly and surprisingly may result in tensile properties showing a viscoelastoplastic behavior matching the target human joint tissue. In preferred embodiments, the chosen textile design is a leno-weave or a knitted structure and the chosen raw material is a benzyl ester of hyaluronic acid. In the same preferred embodiments, the toe region may range between about 0% and about 4% of the tensile strain and an elastic region ranging from about 0% to about 8% of the tensile strain, unexpectedly and surprisingly matching the target human tendon tissue properties.

In some embodiments, the combination of a given textile design with a given raw material can show a maximum load ranging from 40 to 800 N, in preferred embodiments the bioabsorbable textiles can show a maximum load ranging from 50 to 250 N. In some embodiments, the bioabsorbable textiles can show a Young's modulus ranging from 0.1 to 800 MPa, in preferred embodiments the bioabsorbable textiles can show a Young's modulus ranging from 1 to 300 MPa. In some embodiments, the bioabsorbable textiles can show a failure stress ranging from 3 to 20 MPa, in preferred embodiments the bioabsorbable textiles can show a failure stress ranging from 4 to 15 MPa. In some embodiments, the bioabsorbable textiles can show a failure strain ranging from 10 to 70%, in preferred embodiments the bioabsorbable textiles can show a failure strain ranging from 15 to 45%. In some embodiments, the bioabsorbable textiles can show a yield stress ranging from 2 to 50 MPa, in preferred embodiments the bioabsorbable textiles can show a yield stress ranging from 2.5 to 15 MPa. In some embodiments, the bioabsorbable textiles can show a yield strain ranging from 0.5 to 8%, in preferred embodiments the bioabsorbable textiles can show a yield strain ranging from 1.5 to 6.5. In some embodiments, the bioabsorbable textiles can show a yield load ranging from 25 to 300 N, in preferred embodiments the bioabsorbable textiles can show a yield load ranging from 30 to 150 N. In some embodiments, the bioabsorbable textiles can show a stiffness ranging from 10000 to 200000 N/m, in preferred embodiments the bioabsorbable textiles can show a stiffness ranging from 12000 to 80000 N/m. In some embodiments, the bioabsorbable textiles can show an apparent failure strain ranging from 30 to 95%, in preferred embodiments the bioabsorbable textiles can show an apparent failure strain ranging from 40 to 85%. In some embodiments, the bioabsorbable textiles can show an apparent yield strain ranging from 3 to 12%, in preferred embodiments the bioabsorbable textiles can show an apparent yield strain ranging from 5 to 11%. In some embodiments, the bioabsorbable textiles can show an apparent Young's modulus ranging from 1 to 500 MPa, in preferred embodiments the bioabsorbable textiles can show an apparent Young's modulus ranging from 1 to 120 MPa. In some embodiments, the bioabsorbable textiles can show a load at 5 mm ranging from 30 to 160 N, in preferred embodiments the bioabsorbable textiles can show a load at 5 mm ranging from 35 to 140 N. In some embodiments, the bioabsorbable textiles can show an elongation at 50 N ranging from 0.5 to 15 mm, in preferred embodiments the bioabsorbable textiles can show an elongation at 50 N ranging from 1 to 12 mm.

Taken all these data together, the leno-weave or knitted configurations combined together with the use of a benzyl ester of hyaluronic acid, make the bioabsorbable textile suitable for mechanical augmentation of the target joint.

In some embodiments, the combination of a given textile design with a given raw material, for example for lenowave or knitted designs made of a derivative of hyaluronic acid, resulted in mechanically-robust bioabsorbable textiles able to withstand at least up to 2500 loading cycles at physiological stress and frequency values. In preferred embodiments, the cyclic elongation of the bioabsorbable textiles may range from about 2 mm at the first cycle and about 12 mm at $2500^{th}$. In the same preferred embodiments the bioabsorbable textiles show load to failure values after 2500 cycles ranging between 50 N to 250 N.

The combination of a given textile design with a given raw material in some embodiments, for example for leno-wave or knitted designs made of a derivative of hyaluronic acid, results in mechanically-robust bioabsorbable textiles able to show a suture pull-out strength ranging from about 8 N to about 800 N. In preferred embodiments, the suture pull-out strength of the bioabsorbable textiles ranges from about 20 N to about 100 N.

The combination of a given textile design with a given raw material in some embodiments, for example for lenowave or knitted designs made of a derivative of hyaluronic acid, results in bioabsorbable textiles showing the following analytical features: loss on drying ranging from about 1% to about 20%; a percent of esterification of the carboxylic group of hyaluronic acid ranging from about 60% to about 100%; and a percent of a free esterifying group detached from the hyaluronic acid derivative ranging from about 0% to about 0.4%. In preferred embodiments, the bioabsorbable textiles show a loss on drying ranging from about 2% to about 15%; a percent of esterification of the carboxylic group of hyaluronic acid ranging from about 85.0% to about 99.9%; and a percent of a free esterifying group detached from the hyaluronic acid derivative ranging from about 0.01% to about 0.2%.

The combination of a given textile design with a given raw material in preferred embodiments, for example for lenowave or knitted designs made of a derivative of hyaluronic acid, may result in bioabsorbable textiles showing excellent biological properties, such as a cell viability ranging from about 70% to about 100% and an in vitro collagen induction ranging from about 50 to about 150 ug/mg protein whereas the solid, mature collagen portion ranges from about 5 to about 50 ug/mg protein. The bioabsorbable textiles can be prepared as multi-layered or gradient structures incorporating differential mechanical and/or morphological properties in one or more directions.

In some embodiments, a bioabsorbable textile as described herein can be bonded (physically and/or chemically) to one or more additional or same bioabsorbable textiles.

In another aspect the invention relates to a multilayer structure for joint function restoration comprising at least one bioabsorbable textile of the invention.

The multi-layered structure can be tuned to incorporate, for example, a mechanically robust layer in one section to support a morphologically favorable (e.g., for cellular infiltration and proliferation) layer in another section. The multi-layered structure could further be used to incorporate a therapeutic agent in one section (e.g., the lesion side), while omitting the therapeutic agent in another section. Bonding of one bioabsorbable textile can be achieved by numerous methods including mechanical (suturing, tacking, hook and loop, etc.), thermal (conductive heat, convective heat, radiative heat, RF welding, US welding, etc.), chemical (solvent, adhesive, etc.), or a combination of the above methods. In preferred embodiments, a two-layered composite textile is prepared by using solvent (e.g., DMSO, HFIP, DMF, etc.), heat (100-250° C.), and pressure (1-100 MPa) to bond a warp knitted bioabsorbable textile (e.g., HD1) to a nonwoven pad bioabsorbable textile (e.g. non-woven fabric based on HA benzyl ester). The edges of the multi-layered structure can be sealed by means of cauterization (e.g., electrocautery, chemical cautery, hot knife, laser cutting, US welding, RF welding, induction, etc.). In preferred embodiments, the multi-layered composite textile structure is cut and cauterized with a $CO_2$ laser. The multi-layered structure can also be fabricated with one or more through-holes to facilitate passing of medical instruments or devices through the structure (e.g., needles, sutures, suture tapes, anchors, etc.). In some embodiments, the hole or holes can be manufactured mechanically (e.g., blade or punch), chemically (e.g., solvent), or thermally (e.g., hot die, hot blade, laser, US welding, RF welding, etc.). In some embodiments the hole or holes are approximately 0.1-10 mm in diameter. In preferred embodiments, the hole or holes are 0.5-2 mm in diameter. In some embodiments the holes comprise a non-circular profile (e.g., oblong, oval, rectangular, trapezoidal, etc.).

In another aspect the invention relates to the bioabsorbable textile for use in repairing the joint function. Specifically, the invention relates to the bioabsorbable textile of the invention for use in restoring joint function affected by partial thickness tears, small to medium full-thickness tears, large to massive full-thickness tears, acute and chronic/degenerative tears.

In another aspect the invention relates to the bioabsorbable textile of the invention for use in surgery in combination with fixation tools during open, mini-open or arthroscopic repair/augmentation procedures of joint tissue tears.

The textile can hence be used in a method of treatment for restoring the joint function.

The method of the invention comprises the implantation of the bioabsorbable textile in combination with fastening means (such as sutures, and/or pins, and/or tags, and/or suture anchors, and/or bone anchors, and/or staples) during surgical repair/augmentation procedures of joint tissue tears. Specifically, in some embodiments the textile may be delivered in situ after or at the same time the soft tissue tear has been repaired using one or a combination of the fixation tools above mentioned.

The method of the invention refers to open, mini-open or arthroscopic procedures. In some embodiments, the bioabsorbable textile may comprise specific features that improve its surgical deliverability in open, mini-open or arthroscopic settings. It is in the scope of this invention the treatment of partial thickness tears, small to medium full-thickness joint tissue tears; large to massive full-thickness tears acute and chronic/degenerative tears; and interstitial delamination of the fibers comprising the extracellular matrix of the joint tissues.

In some embodiments, the arthroscopic method to treat joint tears in order to restore their function starts by creating an access, which in some preferred embodiments may be posterior, between the glenoid and the humerus that will then be used to insert an arthroscopic guide having a diameter ranging from 5 to 10 mm. From this access, in preferred embodiments an arthroscope is inserted in order to approach the sub-acromial space. In some embodiments, the arthroscopic method may continue by creating one or a plurality of other accesses. In preferred embodiments, these accesses are created in lateral and antero-lateral positions. In some embodiments, the arthroscopic method may continue with the insertion in the joint of a plurality of shuttle wires implantation that are positioned considering the size of the bioabsorbable textile with the aid of a surgical ruler. In preferred embodiments, four to six shuttle wires are used, one for each corner of the bioabsorbable textile and two optional wires positioned at the middle of both edges. In other preferred embodiments, the shuttle wires are delivered and installed only at the musculotendinous junction side while a plurality of fasteners are used at the tendon-to-bone interface selected from a group consisting in suture anchors, staples, screws, and tacks. In preferred embodiments, the bone fasteners are selected from the group consisting in screw-in, interference-fit, tack-in, knotted or knotless fixation devices whose main body is made of a material selected from a group including but not limited to absorbable materials (PLGA, PLA, PCL, etc.) PEEK, titanium, stainless steel, or a combination thereof.

In some embodiments, the arthroscopic method to treat joint tears may continue by marking the bioabsorbable textile to help the end-user to visualize the upper and lower side. In some other embodiments, the bioabsorbable textile may be already pre-marked. In some embodiments, the arthroscopic method to treat joint tears may continue by stitching suture threads at the edges of the bioabsorbable textile by means of a plurality of knots. In preferred embodiments, suture threads with a size of at least zero or higher are used. In preferred embodiments, knots are made in the warp direction. In other preferred embodiments, the bioabsorbable textile may be already pre-sutured with one or with a plurality of suture threads placed at both edges (warp direction) to minimize surgeon's effort and time in the operating room. In some embodiments, suture tapes are used. In some embodiments the arthroscopic method may continue by inserting the textile into the joint through either an incision or by using an arthroscopic cannula from one of the pre-made accesses. In some embodiments, the arthroscopic cannula may have an internal diameter ranging from 6 to 15 mm.

In preferred embodiments, the arthroscopic method to treat joint tears may continue by fixing the bioabsorbable textile to the musculotendinous junction of the target joint, optionally taking advantage of the pre-implanted shuttle wires. In other embodiments, the bioabsorbable textile is fixed at the enthesis side first and then attached to the musculotendinous junction of the target joint. Once the textile is fixed at one side, the arthroscopic method to treat joint tears may end by fixing the other side of the textile to the tendon or to the tendon-to-bone interface of the target joint, optionally by leveraging either the pre-implanted shuttle wires or the pre-implanted bone fasteners. In more preferred embodiments, the bioabsorbable textile delivered in situ with a surgical inserter can be fixed at both ends by using resorbable or non-resorbable fasteners.

In some embodiments, the bone at the interface with the tendon may be optionally decorticated prior to the implantation of the textile. In some embodiments, the bone at the interface may be optionally treated with injectable bone cements. In some embodiments, the sutures fixing the textile to the tendon or to the tendon-to-bone interface may be passed through one or a plurality of pre-drilled bonetunnels. In some other embodiments, the open method to treat joint tears in order to restore their function may start by creating an access by means of a knife with a width ranging from about 1 to about 10 cm. In some embodiments, the open method may continue with the insertion in the joint of a plurality of fasteners that are positioned considering the size of the bioabsorbable textile with the aid of a surgical ruler. In preferred embodiments, four to six fasteners are used, one for each corner of the bioabsorbable textile and two optional wires positioned at the middle of both edges. In other preferred embodiments, resorbable fasteners are positioned and installed only at the musculotendinous junction side while a plurality of non-resorbable fasteners are used at the tendon-to-bone interface selected from a group consisting in suture anchors, staples, screws, and tacks. In preferred embodiments, the bone fasteners are selected from the group consisting in screw-in, interference-fit, tack-in, knotted or knotless fixation devices whose main body is made of a material selected from a group including but not limited to PEEK, titanium, stainless steel, or a combination thereof.

In some embodiments, the open method may continue by stitching suture threads at the edges of the bioabsorbable textile by means of a plurality of knots. In preferred embodiments, suture threads with a size of at least size 0 or higher are used. In preferred embodiments, knots are made in the warp direction. In more preferred embodiments, the bioabsorbable textile may be already pre-sutured with one or with a plurality of suture threads at the two edges of one border (warp direction) to minimize surgeon's effort and time in the operating room. Once suture threads have been stitched onto the bioabsorbable textile, in some embodiments the open method may continue by inserting the textile into the joint through the wide access. In preferred embodiments, the textile is inserted with the pre-stitched sutures facing upwards. In preferred embodiments, a surgical inserter may be used to deploy the bioabsorbable textile in situ.

In preferred embodiments, the open method to treat joint tears may continue by fixing the bioabsorbable textile to the musculotendinous junction of the target joint taking advantage of the pre-implanted shuttle wires. In other embodiments, the bioabsorbable textile is fixed at the enthesis side first and then attached to the musculotendinous junction of the target joint. Once the textile is fixed at one side, the open method to treat joint tears may end by fixing the other side of the textile to the tendon or to the tendon-to-bone interface of the target joint by leveraging either the pre-implanted shuttle wires or the pre-implanted bone fasteners. In more preferred embodiments, the bioabsorbable textile delivered in situ with a surgical inserter can be fixed at both ends by using resorbable or non-resorbable fasteners.

In some embodiments, the bone at the interface with the tendon may be optionally decorticated prior to the implantation of the textile. In some embodiments, the sutures fixing the textile to the tendon or to the tendon-to-bone interface may be passed through one or a plurality of pre-drilled bone tunnels.

EXPERIMENTAL PART

HYALONECT® is a resorbable knitted fabric surgical mesh made of benzyl ester of hyaluronic acid. It is prepared starting from a benzyl ester of hyaluronic acid multifilament 30 tex that is weaved using a circular knitting machine to obtain tubular mesh. The tubular mesh obtained is cut into pieces of the required size. HYALONECT® is intended for use in orthopedic and trauma reconstructive procedures to maintain the relative position of engrafted bone tissue (autograft, allograft, and bone graft substitutes) or bone fragments from comminuted fractures. The mesh is resorbable and suturable and may be fixed to the surgical site of application by means of sutures, or internal bone fixation devices. HYALOFAST® is a biodegradable support for the entrapment of mesenchymal stem cells for the repair of chondral and osteochondral lesions. It is a three-dimensional, nonwoven pad entirely composed of benzyl ester of hyaluronic acid. HYALOFAST® is initially filling the joint tissue defect and temporarily substituting the chondral and osteochondral tissue in the lesion until it is absorbed and replaced by the joint tissue.

GRAFTJACKET™ 5×10 cm, Thickness 0.89-1.40 mm Non-Meshed Standard, Lot #AH101078-085. GraftJacket is an allograft, in particular a non-cross-linked human dermis. Currently, GraftJacket (Wright Medical Technology) is the gold standard in augmentation procedures, for this reason in the following examples is used as a comparison scaffold.

REGENETEN 2.5×3 cm, Thickness 1.0-1.30 mm high porosity reconstituted type I collagen mesh of bovine origin.

EXAMPLES

The following examples further describe and demonstrate four preferred embodiments of the leno-weave bioabsorbable textile (later referred as Design 1, Design 2, Design 3 and Design 4, see Table 1) and five preferred embodiments of the warp-knitted bioabsorbable textile (later referred as High Density Double Bar HD2, Low Density Double Bar LD2, High Density Single Bar HD1, Low Density Single Bar LD1 and High Density Single Bar* HD1*, see Table 1) within the aim of the present disclosure. The examples are given solely for the purpose of illustration and are not be construed as limitations of the present disclosure, as many variations thereof are possible without departing from the spirit and scope of the disclosure.

TABLE 1

Bioabsorbable textile variants

| Bioabsorbable textile | Configuration | Nomenclature | Areal density | Thickness |
|---|---|---|---|---|
| Leno-weave | 17.5 dents per cm | Design 1 | 331 gsm | 0.755 mm |
| | 14 dents per cm | Design 2 | 270 gsm | 0.775 mm |
| | 4 warp yarns per dent | Design 3 | 531 gsm | 0.986 mm |
| | 6 warp yarns per dent | Design 4 | 665 gsm | 1.295 mm |
| Warp-knitted | High Density Double Bar | HD2 | 426 gsm | 0.761 mm |
| | Low Density Double Bar | LD2 | 274 gsm | 0.650 mm |
| | High Density Single Bar | HD1 | 248 gsm | 0.529 mm |
| | Low Density Single Bar | LD1 | 166 gsm | 0.464 mm |
| | High Density Single Bar* | HD1* | 325 gsm | 0.540 mm |

All the bioabsorbable textiles indicated in Table 1 were prepared as indicated in the detailed description for the configurations by starting from a yarn of benzyl ester of hyaluronic acid.

Example 1: Yarn Characteristics

Described herein is the evaluation of yarn characteristics of one preferred embodiment of the yarn comprising the leno-weave bioabsorbable textiles according to the present disclosure.

One preferred embodiment of the yarn comprising the bioabsorbable textiles showed a linear mass density of 65.70±2.84 tex, a breaking strength of 8.32±0.58 N, an extension at break of 5.0±0.9%, an amount of spin finish of 3.58±0.01% w/w, a percentage of esterification of 95.34±0.60%, an amount of free benzyl alcohol lower than the limit of quantification, a loss on drying of 6.55±0.57%, a residual amount of dimethyl sulfoxide of 0.13±0.02%, a residual amount of acetone lower than the limit of quantification, and a residual amount of ethyl alcohol of 0.09±0.04%.

Example 2: Mesh Weave Characteristics

Described herein is the evaluation of mesh weave characteristics of four preferred embodiments of the leno-weave bioabsorbable textiles according to the present disclosure.

One picture of each region (lower, middle, upper) of the specimen in both direction (warp and weft), with a ruler orthogonal aligned respect the side of the sample, was taken with a ZetaLine microscope. The number of yarns per unit length was counted. Three specimens of bioabsorbable textile were analyzed for Design 1 and Design 2, and nine specimens of bioabsorbable textile were analyzed for Design 3 and Design 4.

Warp direction: one preferred embodiment of the bioabsorbable textile showed 18.67±0.87 number of yarns per cm (Design 1), one other preferred embodiment of the bioabsorbable textile showed 15.89±1.45 number of yarns per cm (Design 2), one other preferred embodiment of the bioabsorbable textile showed 29.63±0.63 number of yarns per cm (Design 3) and one other preferred embodiment of the bioabsorbable textile showed 35.11±1.93 number of yarns per cm (Design 4).

Weft direction: one preferred embodiment of the bioabsorbable textile showed 11.33±2.65 number of yarns for cm (Design 1), one other preferred embodiment of the bioabsorbable textile showed 8.44±1.94 number of yarns for cm (Design 2), one other preferred embodiment of the bioabsorbable textile showed 7.79±0.41 number of yarns for cm (Design 3) and one other preferred embodiment of the bioabsorbable textile showed 8.00±0.00 number of yarns for cm (Design 4).

The results show a high value of standard deviation, in particular for weft direction for Design 1 and Design 2, due to the structure of suture pads. In these regions, for Design 1 and Design 2, the bioabsorbable textiles have a more compact structure with a major number of yarns per unit length.

Example 3: Thickness Measurement

Described herein is the evaluation of thickness of four preferred embodiments of the leno-weave bioabsorbable textiles and four preferred embodiments of the knitted bioabsorbable textiles according to the present disclosure.

The thickness was measured following ASTM D1777-96 (2015). The thickness of each leno-weave bioabsorbable textile was measured in three different points (lower, middle, upper) with a Wisamic digital Thickness gauge. Three specimens of bioabsorbable textile were analyzed for Design 1 and Design 2, nine specimens of bioabsorbable textile were analyzed for Design 3 and Design 4.

One preferred embodiment of the leno-weave bioabsorbable textiles showed 0.755±0.009 mm (Design 1), one other preferred embodiment of the leno-weave bioabsorbable textiles showed 0.775±0.015 mm (Design 2), one other preferred embodiment of the leno-weave bioabsorbable textiles showed 0.986±0.032 mm (Design 3), one other preferred embodiment of the leno-weave bioabsorbable textiles showed 1.295±0.035 mm (Design 4).

The thickness of each knitted bioabsorbable textile was measured in one point (middle) with a Wisamic digital Thickness gauge.

One preferred embodiment of the knitted bioabsorbable textiles showed about 0.761 mm (HD2), one other preferred embodiment of the knitted bioabsorbable textiles showed about 0.65 mm (LD2), one other preferred embodiment of the knitted bioabsorbable textiles showed about 0.529 mm (HD1), one other preferred embodiment of the knitted bioabsorbable textiles showed about 0.464 mm (LD1), one other preferred embodiment of the knitted bioabsorbable textiles showed about 0.540 mm (HD1*).

Example 4: Areal Density Measurement

Described herein is the evaluation of areal density of four preferred embodiments of the leno-weave bioabsorbable textiles and four preferred embodiments of the knitted bioabsorbable textiles according to the present disclosure.

The length and width of each prototypes was measured in three different regions (lower, middle, upper) with a Maurer digital caliper. Each specimen was weighted by an analytical balance. Three specimens of leno-weave bioabsorbable textile were analyzed for Design 1 and Design 2, nine specimens of leno-weave bioabsorbable textile were analyzed for Design 3 and Design 4.

One preferred embodiment of the leno-weave bioabsorbable textiles showed a mesh density of 330.8±0.9 gsm (Design 1), one other preferred embodiment of the leno-weave bioabsorbable textiles 270.3±1.3 gsm (Design 2), one other preferred embodiment of the leno-weave bioabsorbable textiles 531.2±8.7 gsm (Design 3), one other preferred embodiment of the leno-weave bioabsorbable textiles 665.4±7.8 gsm (Design 4).

The length and width of each prototypes was measured on one side (middle) with a Maurer digital caliper. Each specimen was weighted by an analytical balance.

One preferred embodiment of the knitted bioabsorbable textiles showed a mesh density of about 426 gsm (HD2), one other preferred embodiment of the knitted bioabsorbable textiles about 274 gsm (LD2), one other preferred embodiment of the knitted bioabsorbable textiles about 248 gsm (HD1), one other preferred embodiment of the knitted bioabsorbable textiles 166 gsm (LD1), one other preferred embodiment of the knitted bioabsorbable textiles 325 gsm (HD1*).

Example 5: Swelling Measurement

Described herein is the evaluation of swelling of four preferred embodiments (referred as Design 1, Design 2, Design 3 and Design 4) of the leno-weave bioabsorbable textiles according to the present disclosure. The samples were immersed with 15 ml of PBS in petri dishes at 37° C. to simulate the physiological environment. At different time points, 1 h, 24 h and 48 h, the samples were blotted on paper to eliminate the excess PBS, and then weight and dimensions were measured. In particular, the length and width of each embodiment of the bioabsorbable textile were measured in three different regions (lower, middle, upper) with a Maurer digital caliper. The thickness was measured following ASTM D1777-96(2015). The thickness of each embodiment of the bioabsorbable textile was measured in three different points (lower, middle, upper) with a Wisamic digital Thickness gauge. Each sample was weighted by an analytical balance. Three specimens of each sample were analyzed. The swelling % was calculated following equation:

$$Sw\ \% = \frac{Ws - Wi}{Wi} * 100$$

Ws is the weight of swelled specimen and Wi is the initial weight of dry specimen.

Figure 3A:
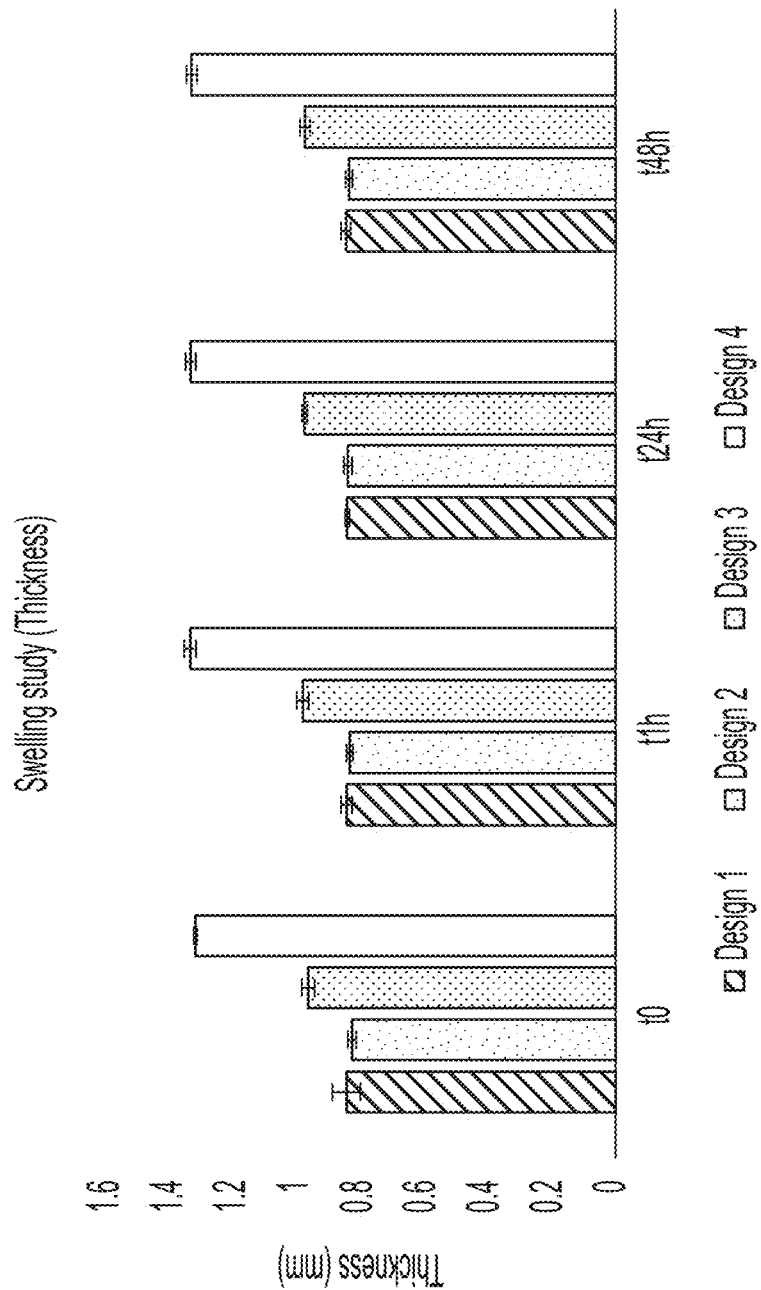
FIG. 3 shows the swelling behavior of four preferred embodiments of the textile of the invention, with reference to FIG. 3A) thickness, FIG. 3B) volume and FIG. 3C) percentage as explained in Example 5.
Figure 3B:
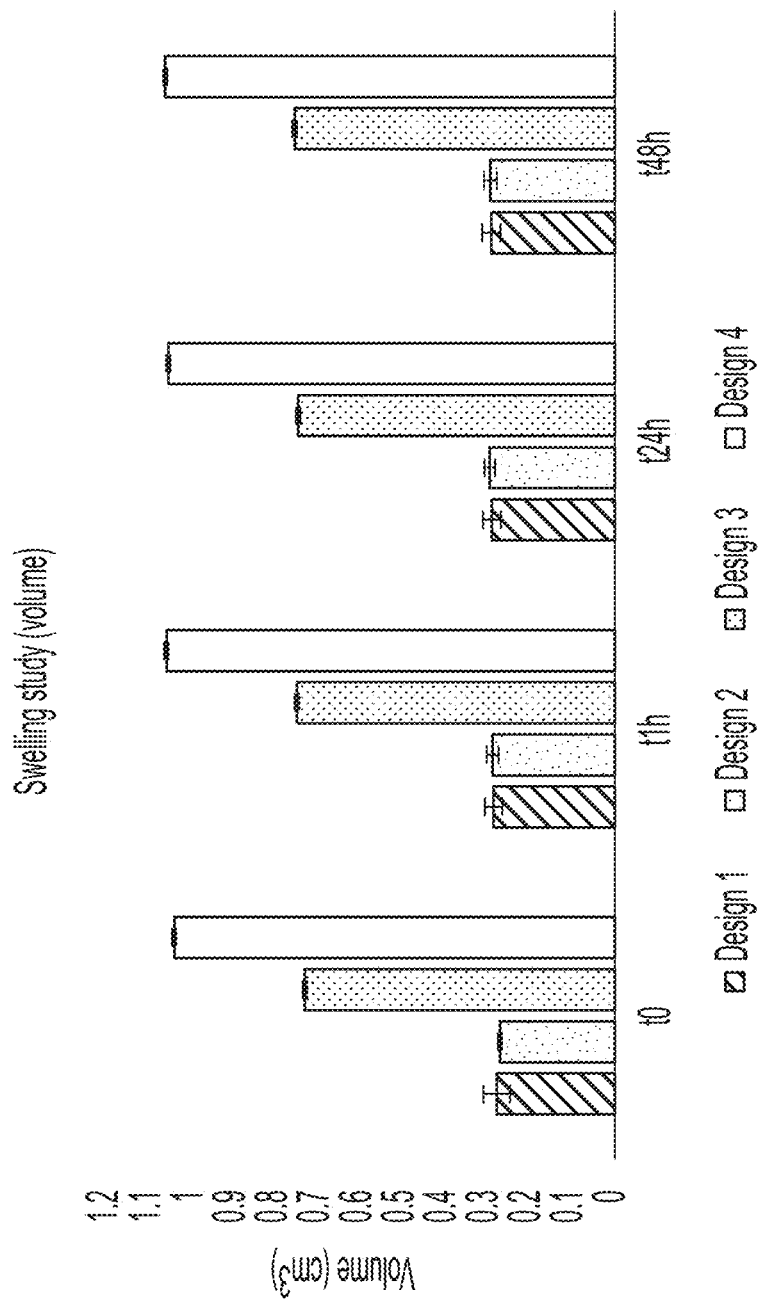

The preferred embodiments of the bioabsorbable textiles did not show an increase or decrease in thickness or volume between swelled and dry conditions, moreover the dimensions did not change during the time of the experiment (FIG. 3A and FIG. 3B).

Figure 3C:
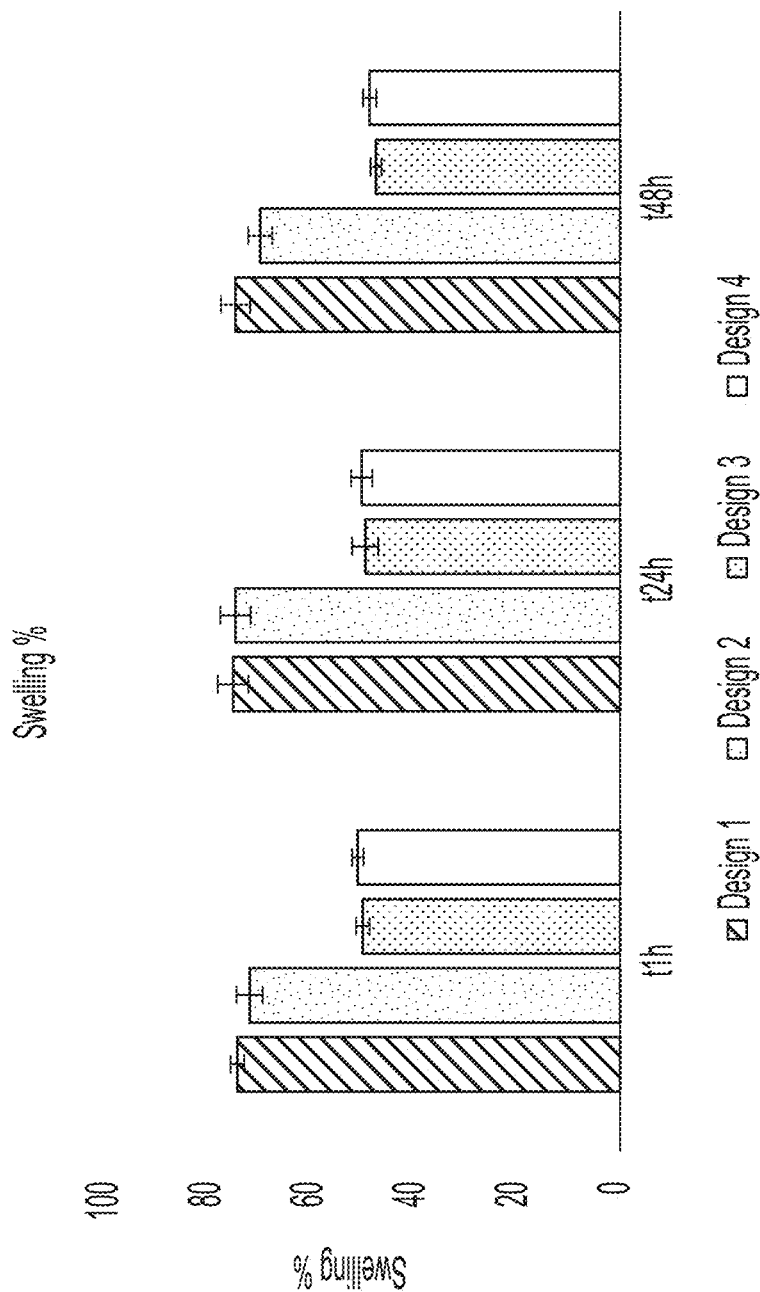
Figures 4A, 4B:
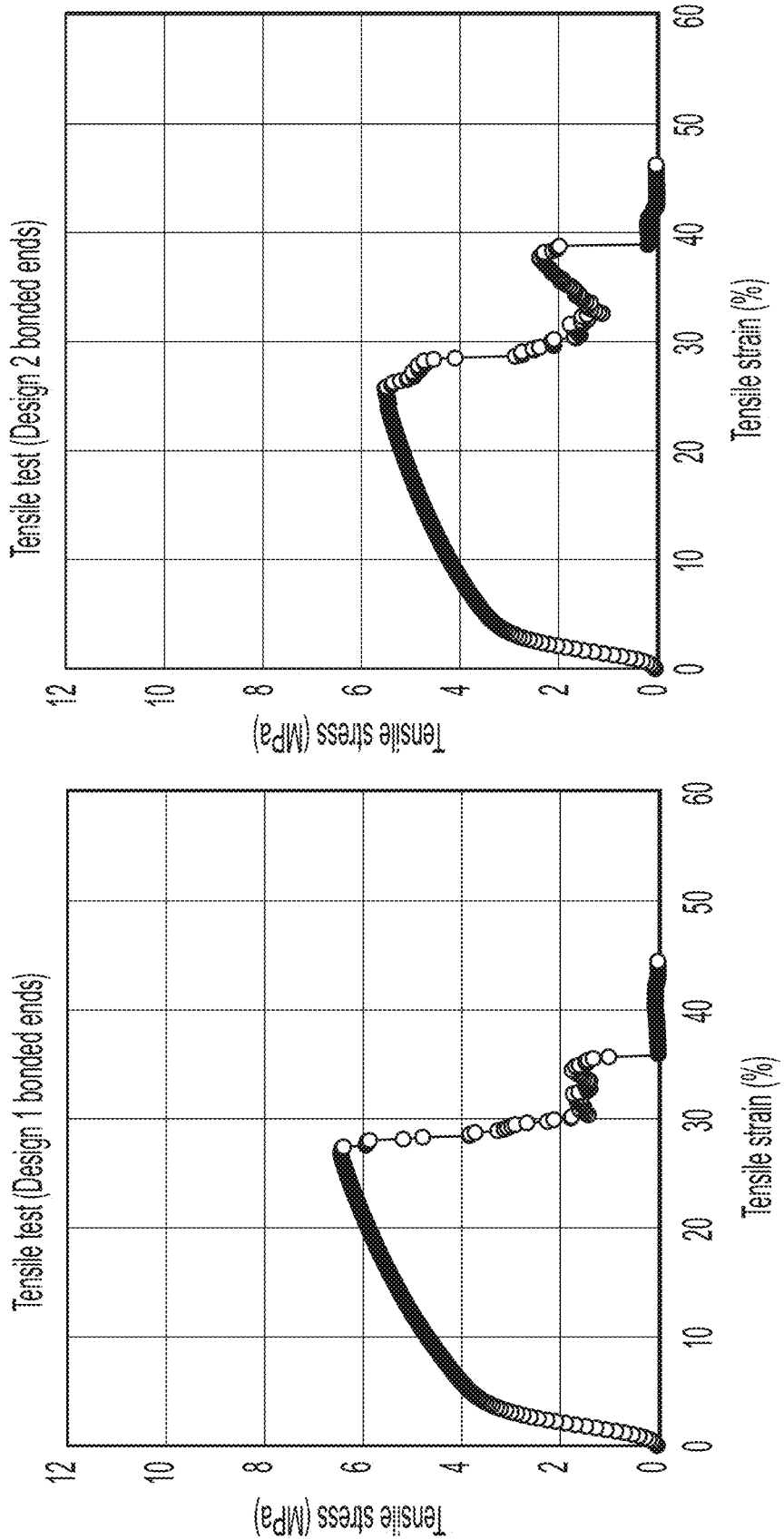
FIG. 4A, FIG. 4B, FIG. 4C and FIG. 4D show the tensile behavior comparison between four preferred embodiments of the textile of the invention as explained in Example 7.
Figures 4C, 4D:
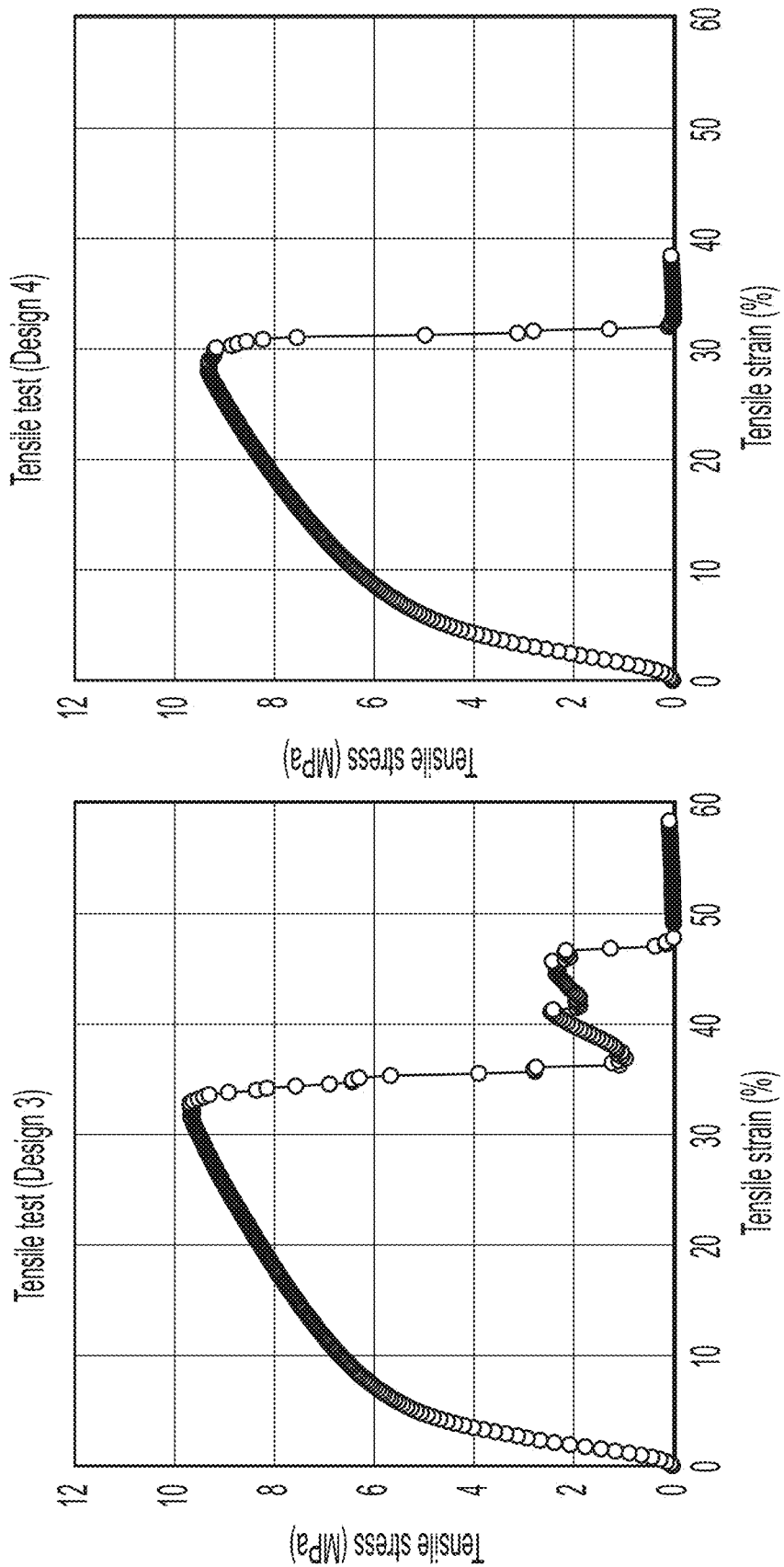

Instead, Design 1 and Design 2 showed a swelling % of about 75% after 1 h in PBS and this value did not change during the experiment (FIG. 3C), Design 3 and Design 4 showed a swelling % of about 50% after 1 h in PBS and this value did not change during the experiment (FIG. 3C).

Example 6: Porosity and Pore Size Determination

Described herein is the evaluation of pore size of two preferred embodiment of the leno-weave bioabsorbable textiles according to the present disclosure.

The pore dimensions (macroporosity) were designed before production step. To analyze also the presence of micropores (inter and intra yarn porosity) a mercury intrusion porosimetry test was performed. Pore size measurement was performed by a Thermo Finningan (Waltman, USA) Pascal 140 e 240. The specimens were dried at 105° C. for 24 hours. Three specimens of each sample were analyzed. The results are related to the pores with a diameter <116 μm (higher limit of the mercury intrusion porosimeter used).

One preferred embodiment of the bioabsorbable textiles showed an accessible porosity of 27.67±1.58%, a total pore volume of 463.65±29.55 mm$^3$/g, an average pore diameter of 3000 nm, and a median pore diameter of 39100 nm (Design 1) instead one other preferred embodiment of the bioabsorbable textiles showed an accessible porosity of 25.70±2.94%, a total pore volume of 461.03±61.71 mm$^3$/g, an average pore diameter of about 5700 nm, and a median pore diameter of 45800 nm (Design 2).

This porous structure of the bioabsorbable textiles is suitable for allowing cell migration and proliferation, so ultimately providing biological augmentation to the target joint tissue.

Example 7: Tensile Strength and Device Stiffness

Described herein is the evaluation of tensile strength and device stiffness of four preferred embodiment of the leno-weave bioabsorbable textiles according to the present disclosure.

Tensile strength and device stiffness were calculated following ASTM D5034-09. The specimens (6 for Design 1 and Design 2; 9 for Design 3 and Design 4) were immersed 1 hour in PBS at 37° C. to simulate the physiological environment. The test was performed by an Instron 3345 Tensile testing apparatus with a load cell of 5 kN. The extension test was performed at 60 mm/min after a pre-load (until 0.4 N) at 10 mm/min. A gauge length of 3.5 cm for Design 1 and Design 2 and a gauge length of 3 cm for Design 3 and Design 4 was settled.

Tensile test was performed on Design 1 and Design 2 with and without bonded ends.

Preferred embodiments of the bioabsorbable textiles showed a mechanical behavior comparable to infraspinatus tendon (FIG. 4A, FIG. 4B, FIG. 4C and FIG. 4D). Prototypes showed a very short toe region and an elastic region in the first part of Stress vs Strain curve.

The mechanical properties of the four different bioabsorbable textiles are summarized in the following tables (Table 2 A, 1B and 1C).

TABLE 2

Mechanical properties of four different embodiments of the bioabsorbable textiles with:
A) Design 1 and Design 2 open ends; B) Design 1 and Design 2 bonded ends;
C) Design 3 and Design 4

A)

| | Young's modulus [MPa] | Failure stress [MPa] | Failure strain [%] | Max. Load [N] | Yield Stress [Mpa] | Yield strain [%] | Yield Load [N] | Stiffness [N/m] |
|---|---|---|---|---|---|---|---|---|
| Design 2 | 187.43 ± 18.05 | 6.12 ± 0.40 | 25.23 ± 2.11 | 59.54 ± 0.62 | 3.73 ± 0.24 | 3.43 ± 0.29 | 36.25 ± 1.25 | 22491.83 ± 83 |
| Design 1 | 189.39 ± 12.08 | 6.86 ± 0.33 | 26.74 ± 0.89 | 71.58 ± 0.84 | 4.07 ± 0.09 | 3.65 ± 0.37 | 42.57 ± 1.42 | 25002.25 ± 891.30 |
| | p > 0.05 | p < 0.05 | p > 0.05 | p < 0.05 | p < 0.05 | p > 0.05 | p < 0.05 | p > 0.05 |

| | | | | | Apparent Young's modulus [Mpa] | Apparent Failure strain [%] | Apparent yield strain [%] |
|---|---|---|---|---|---|---|---|
| Design 2 | | | | | 85.47 ± 5.95 | 53.54 ± 4.13 | 7.14 ± 0.68 |
| Design 1 | | | | | 91.71 ± 4.99 | 52.68 ± 4.70 | 7.19 ± 0.74 |
| | | | | | p > 0.05 | p > 0.05 | p > 0.05 |

TABLE 2-continued

Mechanical properties of four different embodiments of the bioabsorbable textiles with:
A) Design 1 and Design 2 open ends; B) Design 1 and Design 2 bonded ends;
C) Design 3 and Design 4

B)

|  | Young's modulus [MPa] | Failure stress [MPa] | Failure strain [%] | Max. Load [N] | Yield Stress [Mpa] | Yield strain [%] | Yield Load [N] | Stiffness [N/m] |
|---|---|---|---|---|---|---|---|---|
| Design 2 | 132.37 ± 3.58 | 5.89 ± 0.33 | 27.27 ± 2.55 | 57.22 ± 1.22 | 3.31 ± 0.19 | 3.88 ± 0.30 | 31.75 ± 0.84 | 16206.98 ± 1263.73 |
| Design 1 | 116.13 ± 26.03 | 5.96 ± 0.43 | 25.99 ± 2.87 | 65.84 ± 1.93 | 3.24 ± 0.26 | 4.29 ± 0.50 | 34.67 ± 3.21 | 16540.67 ± 3133.94 |
|  | $p > 0.05$ | $p < 0.05$ | $p > 0.05$ | $p < 0.05$ | $p > 0.05$ | $p > 0.05$ | $p < 0.05$ | $p > 0.05$ |

|  | Apparent Young's modulus [Mpa] | Apparent Failure strain [%] | Apparent yield strain [%] |
|---|---|---|---|
| Design 2 | 62.89 ± 4.38 | 55.71 ± 2.72 | 7.81 ± 0.92 |
| Design 1 | 56.35 ± 12.30 | 51.05 ± 6.27 | 8.28 ± 1.02 |
|  | $p > 0.05$ | $p > 0.05$ | $p > 0.05$ |

C)

|  | Young's modulus [MPa] | Failure stress [MPa] | Failure strain [%] | Max. Load [N] | Yield Stress [Mpa] | Yield strain [%] | Yield Load [N] | Stiffness [N/m] |
|---|---|---|---|---|---|---|---|---|
| Design 3 | 149.32 ± 10.50 | 9.44 ± 0.27 | 30.98 ± 1.74 | 141.31 ± 1.90 | 4.32 ± 0.21 | 4.32 ± 0.21 | 71.7 ± 1.88 | 42992.99 ± 1680.82 |
| Design 4 | 119.43 ± 4.32 | 9.24 ± 0.36 | 29.10 ± 1.56 | 184.74 ± 4.05 | 4.73 ± 0.19 | 5.43 ± 0.26 | 94.63 ± 2.84 | 45480.90 ± 1768.78 |
|  | $p > 0.05$ | $p < 0.05$ | $p > 0.05$ | $p < 0.05$ | $p > 0.05$ | $p > 0.05$ | $p < 0.05$ | $p > 0.05$ |

|  | Apparent Young's modulus [Mpa] | Apparent Failure strain [%] | Apparent yield strain [%] |
|---|---|---|---|
| Design 3 | 87.57 ± 4.95 | 53.40 ± 2.85 | 7.44 ± 0.33 |
| Design 4 | 68.62 ± 2.57 | 50.74 ± 2.97 | 9.46 ± 0.40 |
|  | $p > 0.05$ | $p > 0.05$ | $p > 0.05$ |

Figure 5:
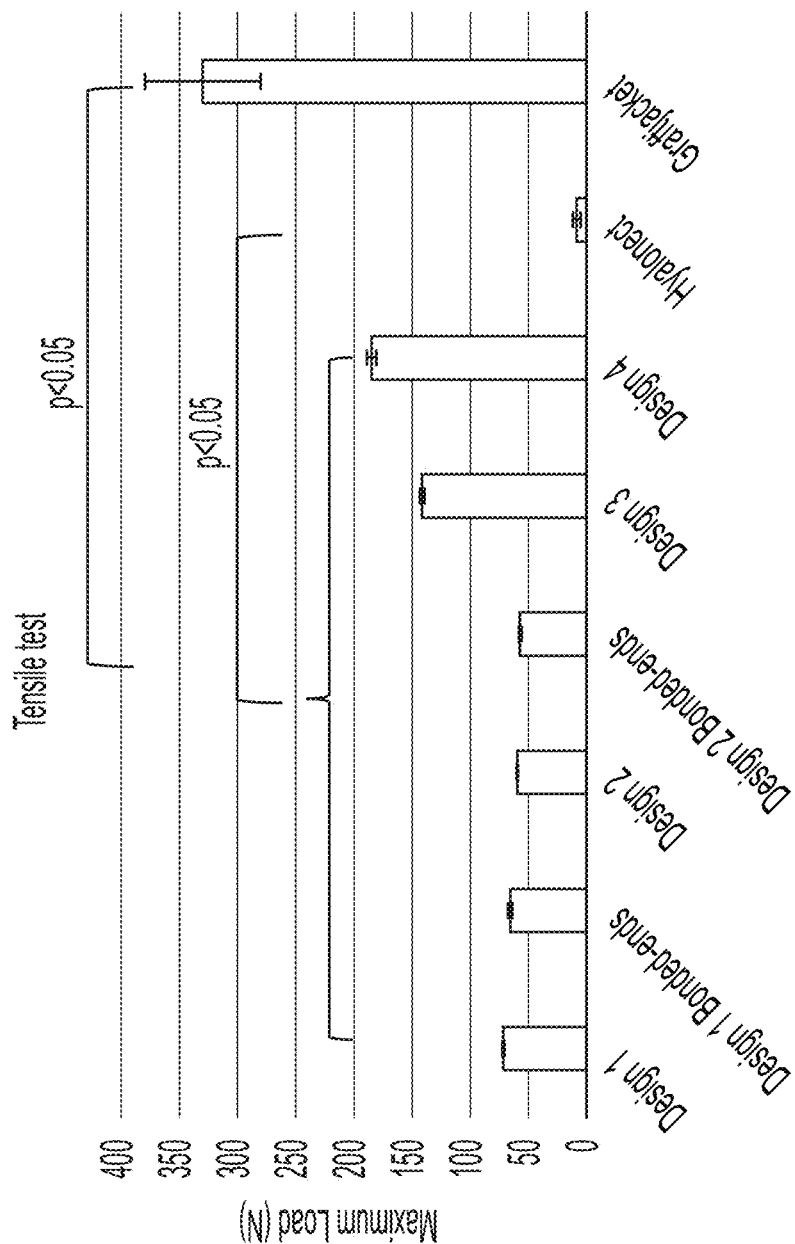
FIG. 5 shows the Maximum Load comparison among different textile configurations of the invention and two comparative devices as explained in Example 7.

Leno-weave bioabsorbable textiles showed higher Maximum load (or failure load) than Hyalonect but lower than GraftJacket (FIG. 5).

However, GraftJacket showed a long toe region (FIG. 6F), as also reported in literature. GraftJacket indeed reached the peak value of load after long extension, conversely to what observed in the native supraspinatus tendon making the properties not relevant for the application.

From the tensile test, elongation at 50 N and load at 5 mm were calculated. These are physiologically-important parameters, as elongation at 50 N is the physiologic load to which an augmentation device is exposed to (Aurora, 2010), while load at 5 mm elongation is the estimated maximum permissible retraction of tendon at the repair site before to lose repair continuity (Hughes, 1996; Burkhart, 1997). An ideal device for rotator cuff repair should show short elongation at 50 N (within 5-10 mm) (Burkhart, 1997) and high load at 5 mm elongation (>50 N).

Figures 6A, 6B:
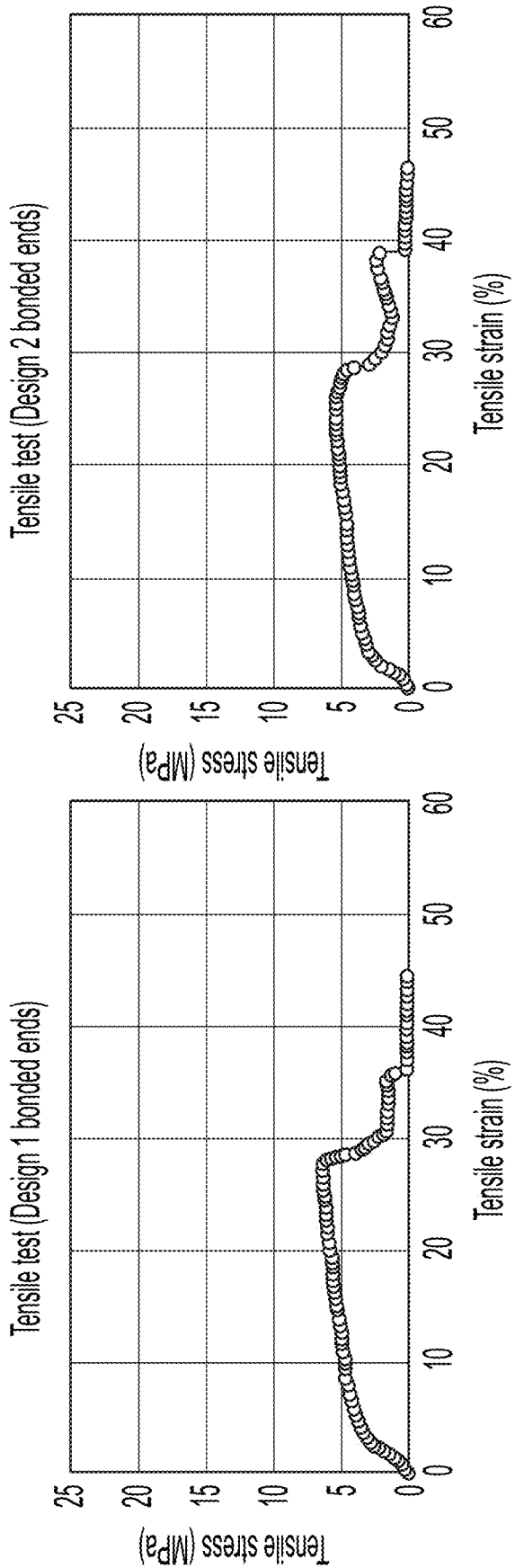
FIG. 6A, FIG. 6B, FIG. 6C and FIG. 6D show the tensile behavior comparison among four preferred embodiments of the textile of the invention.
Figures 6C, 6D:
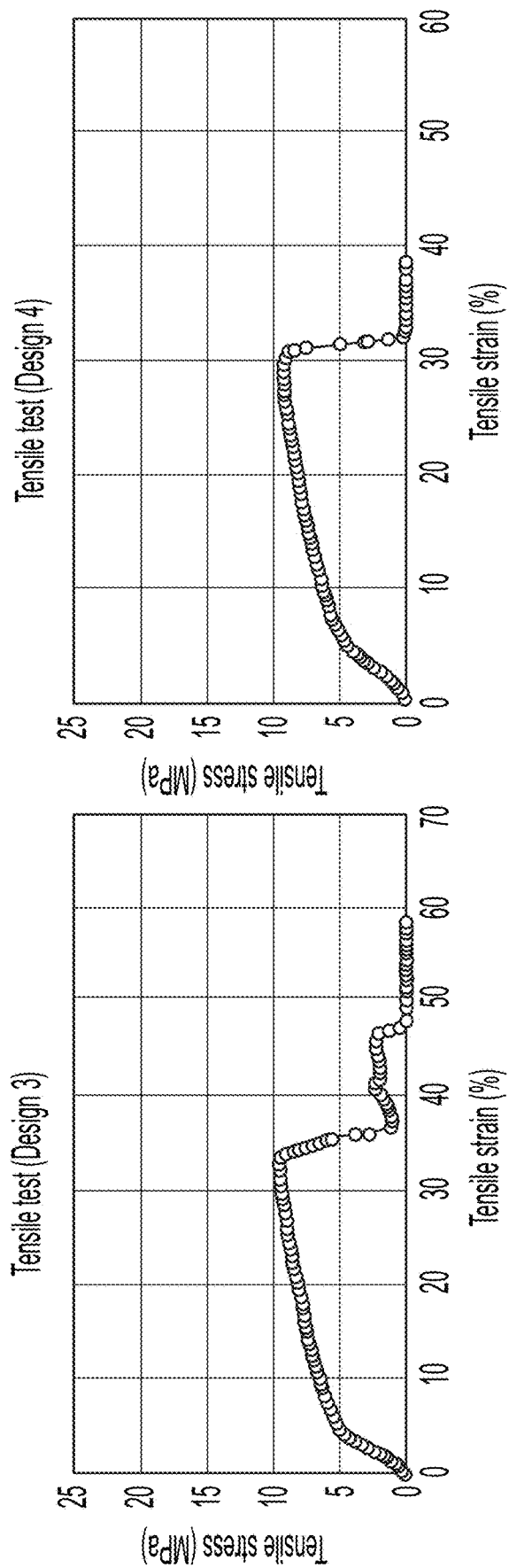
Figures 6E, 6F:
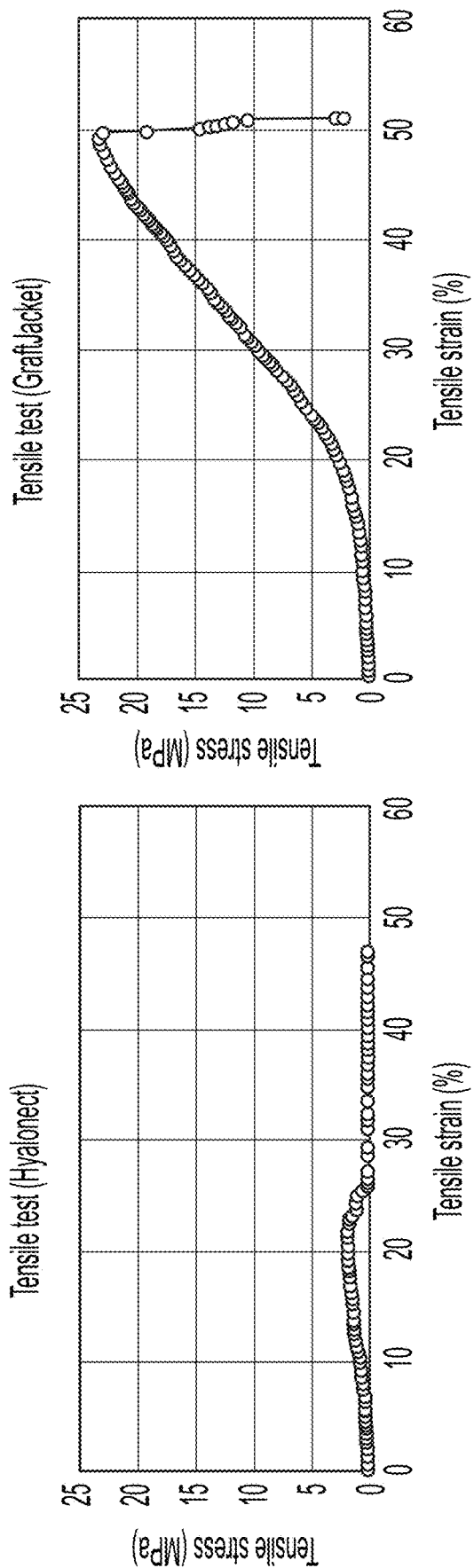
FIG. 6E and FIG. 6F show the tensile behaviour of two comparative devices as explained in Example 7.
Figure 7A:
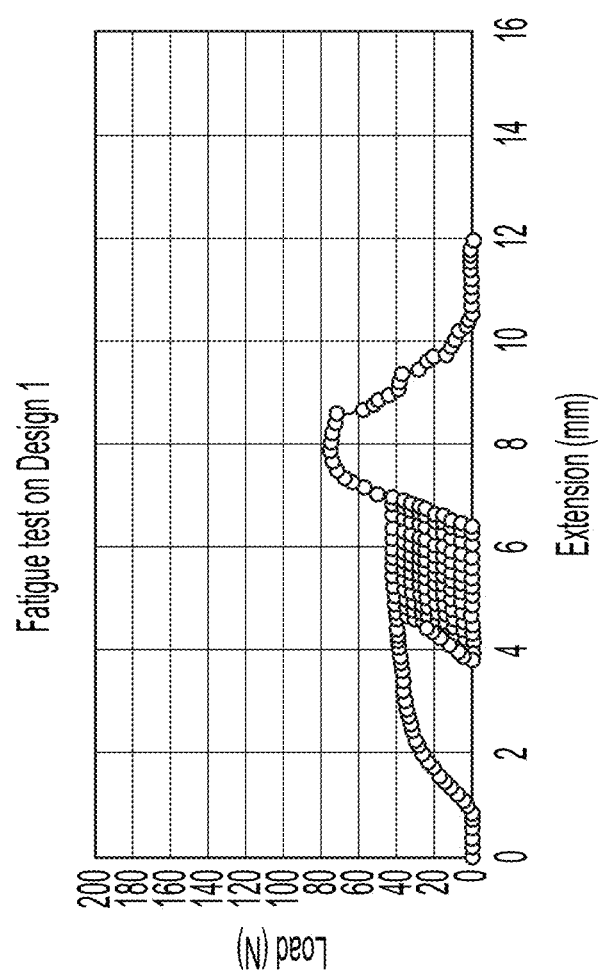
FIG. 7A, FIG. 7B, FIG. 7C and FIG. 7D show the fatigue behavior comparison between four preferred embodiments of the textile of the invention as explained in Example 8.
Figure 7B:
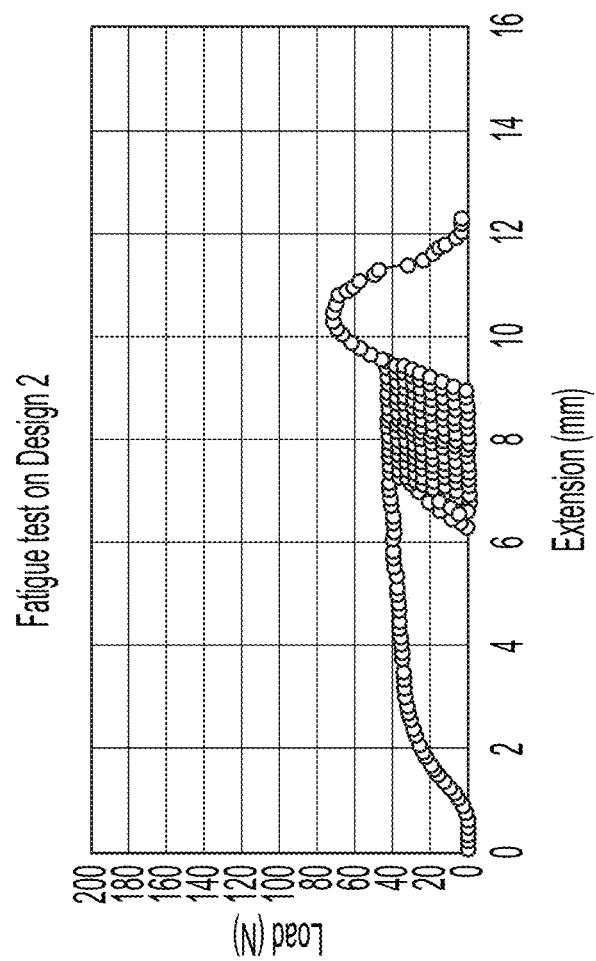
Figure 7C:
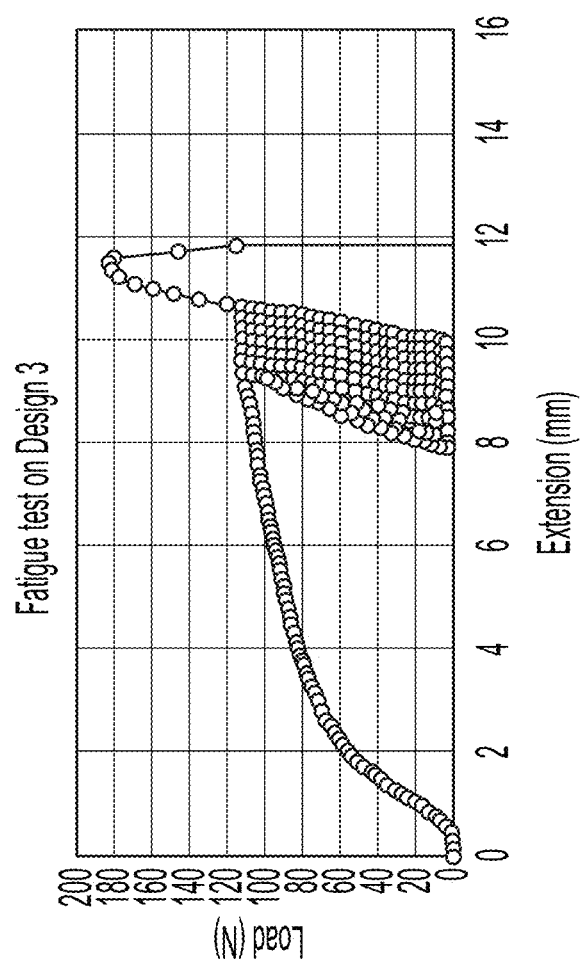
Figure 7D:
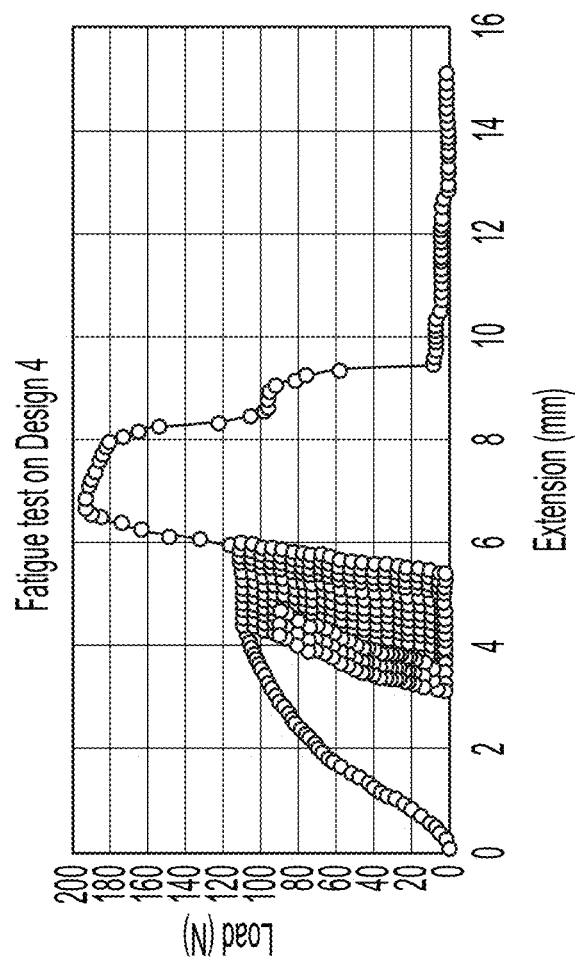

As shown in FIG. 6F GraftJacket showed low load values at short extensions. For Hyalonect, it is impossible to calculate the elongation at 50 N as it could not bear such mechanically-demanding loads. Conversely, the bioabsorbable textiles in all conditions (with and without bonded ends) showed values of elongation at 50 N and load at 5 mm typical of an ideal device for augmentation (Aurora, 2010; Hughes, 1996; Burkhart, 1997).

TABLE 3

Values of load at 5 mm and elongation at 50N

|  | Load at 5 mm [N] | Elongation at 50N [mm] |
|---|---|---|
| Design 1 | 50.00 ± 0.67 | 5.08 ± 0.29 |
| Design 2 | 42.85 ± 1.48 | 9.27 ± 0.94 |
| Design 1 Bonded ends | 43.85 ± 2.58 | 7.60 ± 1.22 |
| Design 2 Bonded ends | 38.98 ± 0.51 | 11.73 ± 0.57 |
| Design 3 | 97.84 ± 1.05 | 1.40 ± 0.07 |
| Design 4 | 123.63 ± 1.78 | 1.44 ± 0.09 |
| GraftJacket | 5.87 ± 0.37 | 12.70 ± 0.14 |
| Hyalonect | 3.02 ± 1.98 |  |

Example 8: Fatigue Test

Described herein is the fatigue test of four preferred embodiments of the leno-weave bioabsorbable textiles according to the present disclosure.

A fatigue test was performed to simulate physiological conditions according to ASTM D3479/D3479M-12 and Amit Aurora et al., 2011 paper (Aurora, 2011). The specimens (3 for each prototype) were immersed 1 hour in PBS at 37° C. to simulate the physiological environment. The test was performed by an Instron 3345 Tensile testing apparatus with a load cell of 100 N for Design 1 and Design 2, with a load cell of 5 kN for Design 3 and Design 4. Fatigue loading was applied for 2500 cycles at 15 mm/min ranged from 1.2 N (2% of lower Maximum load obtained by tensile test) to 43 N (60% of higher Maximum load obtained by tensile test) after an initial ramp at 10 mm/min until 1.2 N for Design 1 and Design 2 and for 2500 cycles at 15 mm/min ranged from 2.8 N (2% of lower Maximum load obtained by tensile test) to 110.8 N (60% of higher Maximum load obtained by tensile test) after an initial ramp at 10 mm/min until 2.8 N for Design 3 and Design 4. The compressed air was set to around 5.5 bar and the gauge length to 3.5 cm for Design 1 and Design 2 and to 3 cm for Design 3 and Design 4. After the cyclic step, an absolute ramp at 60 mm/min was performed until 98 N or when the sample is broken for Design 1 and Design 2 and until 250 N or when the sample is broken for Design 3 and Design 4. The time of the entire test was about 3-4 hours and during the analysis, the specimens were kept wet with PBS solution at 37° C.

Examples of Load vs extension curve obtained after fatigue test were reported in FIG. 7A, FIG. 7B, FIG. 7C and FIG. 7D.

The scaffolds were able to withstand the 2500 loading cycles projected for the early post-operative period (Aurora, 2011).

The four different embodiments of the bioabsorbable textiles show load to failure values after 2500 cycles of 75.29±0.16 N (Design 1), 70.86±0.80 N (Design 2), 189.56±17.33 N (Design 3) and 190.05±3.35 N (Design 4).

Cyclic elongation of the first and $2500^{th}$ cycle, defined as the displacement between the valley at the end of the nth cycle and the valley at the beginning of the first cycle (Aurora, 2011) were calculated. One preferred embodiment of the bioabsorbable textiles showed a cyclic elongation at the first cycle of 2.77±0.33 mm and at $2500^{th}$ cycle of 5.52±0.01 mm (Design 1), one other preferred embodiment of the bioabsorbable textiles showed a cyclic elongation at the first cycle of 5.07±0.45 mm and at 2500th cycle of 7.49±0.64 mm (Design 2), one other preferred embodiment of the bioabsorbable textiles showed a cyclic elongation at the first cycle of 7.36±0.08 mm and at $2500^{th}$ cycle of 9.50±0.05 mm (Design 3), one other preferred embodiment of the bioabsorbable textiles showed a cyclic elongation at the first cycle of 2.81±0.23 mm and at $2500^{th}$ cycle of 4.91±0.25 mm (Design 4). A device for rotator cuff augmentation should limit retraction of the tendon from the bone at the repair site in the range between 5-10 mm (maximum permissible retraction of the tendon from bone without lose repair continuity) (Burkhart, 1997). Considering the obtained data, at least one of the preferred embodiments of the bioabsorbable textiles, even during fatigue test, showed a mechanical behavior that matched the requirements for an ideal device for rotator cuff repair.

Example 9: Suture Pull-Out Strength

Described herein is the evaluation of suture pull-out strength of four preferred embodiment of the leno-weave bioabsorbable textiles and of one preferred embodiment of the knitted bioabsorbable textiles according to the present disclosure.

Suture retention was calculated following a procedure slightly modified from the one described in Barber et al, 2006.

A single 2-0 sterile FiberWire® suture was passed through the textile in a horizontal mattress pattern. Each point of suture was set at one third of sample width apart and at ⅓ of sample width from the other suture point, and suture was carried out to a length of 6 cm from the textile for Design 1, Design 2, Hyalonect and GraftJacket (FIG. 8A and FIG. 8B).

1 Ethilon black monofilament nylon from Ethicon® suture was passed through the textile in a horizontal mattress pattern under the suture pad. The suture was placed 5 mm from the edge, and suture was carried out to a length of 6 cm from the textile for Design 3 and Design 4 according to Barber et al., 2006 (FIG. 8C).

Figure 8D:
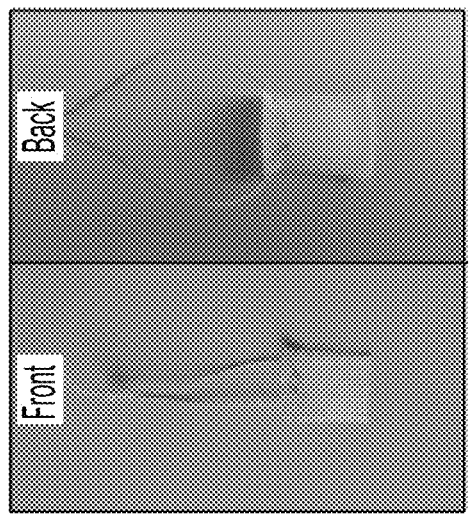
FIG. 8 shows in FIG. 8A) Suture technique on Design 1 and Design 2 (not folded)
in FIG. 8B) Suture technique on Design 1 and Design 2 (folded)
in FIG. 8C) Suture technique on Design 3 and Design 4; and in FIG. 8D) Suture technique on HD1* as explained in Example 9.
Figure 8C:
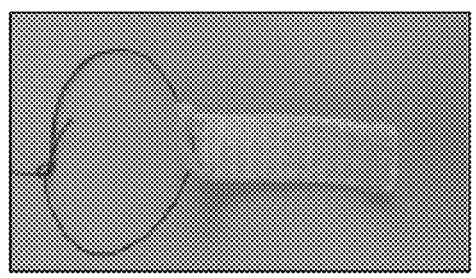
Figure 8B:
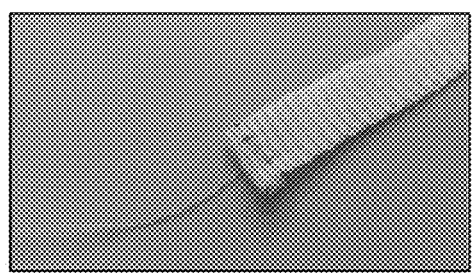
Figure 8A:
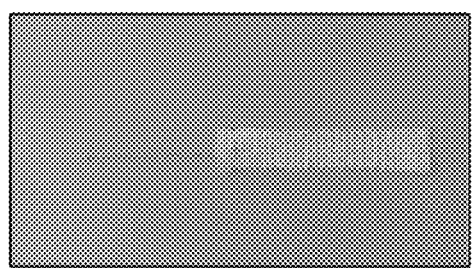

FiberWire 2/5 metric Braided Polyblend Suture Blue with 2 Tapered Needles from Arthrex® suture was passed through the textile in a horizontal mattress pattern 5 mm from the edge, and suture was carried out to a length of 6 cm from the textile for HD1* according to Barber et al., 2006 (FIG. 8D).

The specimens were put 1 hour in PBS at 37° C. to mimic surgical scenario. The test was performed by an Instron 3345 Tensile testing apparatus with a load cell of 100 N for Design 1, Design 2 and HD1*, with a load cell of 5 kN for Design 3 and Design 4. The suture fiber was clamped in the upper clamp. The extension test was performed at 60 mm/min after a pre-load at 10 mm/min until 0.2 N for Design 1 and Design 2. The extension test was performed at 12.5 mm/min after a pre-load at 10 mm/min until 0.2 N for Design 3, Design 4 and HD1*.

The test was performed with the suture pads folded (3 specimens for prototypes) and not folded (3 specimens for each embodiment of the bioabsorbable textile) for Design 1 and Design 2 (FIG. 8A and FIG. 8B). For Design 3 and Design 4, the test was performed on 8 specimens. The HD1* was tested in both directions, machine and transevers (N=5 for each direction), to study if the material exhibits anisotropic or isotropic behavior.

Figure 9:
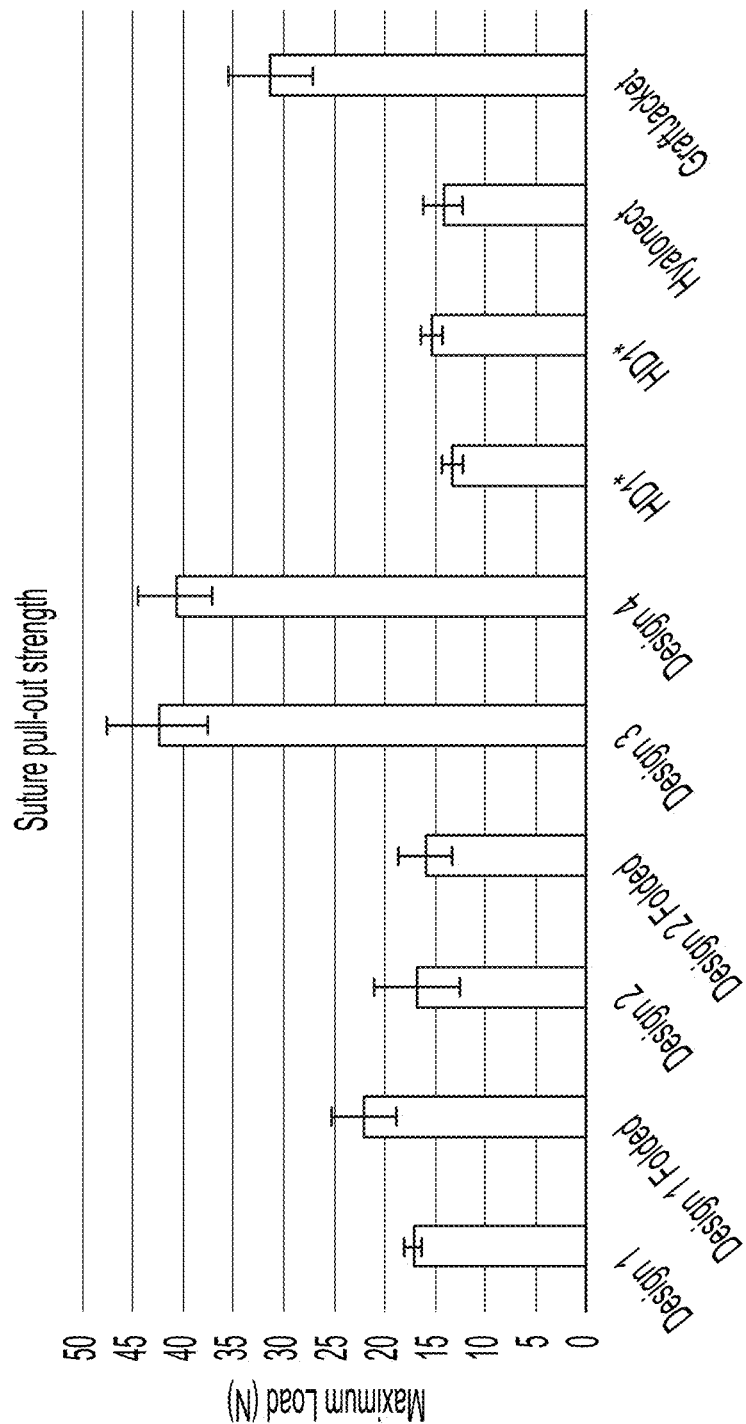
FIG. 9 shows a suture pull-out strength comparison among the preferred embodiments of the textile of the invention in different configurations as explained in Example 9.

The data were summarized in the FIG. 9 and Table 4.

TABLE 4

| | | | | | | | | | |
|---|---|---|---|---|---|---|---|---|---|
| Suture pull-out strength (N) | | | | | | | | | |
| Design 1 | Design 1 Folded | Design 2 | Design 2Folded | Design 3 | Design 4 | HD1* (one direction) | HD1* (other direction) | Hyalonect | GraftJacket Thin |
| 17.17 ± 0.72 | 22.00 ± 3.23 | 16.84 ± 4.30 | 15.88 ± 2.64 | 42.47 ± 5.01 | 40.79 ± 3.76 | 13.29 ± 1.02 | 15.26 ± 1.01 | 14.22 ± 1.84 | 31.33 ± 4.09 |

Example 10: Loss on Drying Evaluation

Described herein is the evaluation of loss on drying of four preferred embodiment of the leno-weave bioabsorbable textiles and one preferred embodiment of knitted bioabsorbable textile according to the present disclosure. The tested textiles of this example were those reported in Table 1.

The loss on drying was calculated measuring the weight of the specimen at the beginning and after drying the specimen (n=1) for 2 hours in oven at 105° C.

One preferred embodiment of the bioabsorbable textiles showed a loss on drying of 9.11% (Design 1), one other preferred embodiment of the bioabsorbable textiles showed a loss on drying of 8.86% (Design 2), one other preferred embodiment of the bioabsorbable textiles showed a loss on drying of 11.77% (Design 3), one other preferred embodiment of the bioabsorbable textiles showed a loss on drying of 10.55% (Design 4), one preferred embodiment of the bioabsorbable textiles showed a loss on drying of about 10.23% (HD1*).

Example 11: Determination of Percentage of Esterification

Described herein is the evaluation of percentage of esterification of four preferred embodiments of the leno-weave bioabsorbable textiles and one preferred embodiment of knitted bioabsorbable textile according to the present disclosure. The tested textiles of this example were those reported in Table 1. The percentage of esterification was determined using HPLC 1260 Infinity Binary Pump equipped with an Infinity Poroshell 120 EC-C18 4.6×100 mm column. The mobile phase was a mixture of highly purified water/acetonitrile 50/50, a flow rate of 1 ml/min, an injection volume of 20 µl, a column temperature of 30° C. and a detection wavelength of 254 nm were chosen.

A calibration curve with benzyl alcohol was prepared.

Around 100 mg of sample (n=1) were treated with 10 mL of 0.1M NaOH solution at 60° C. for about 60 minutes for Design 1 and design 2 and for about 90 minutes for Design 3 and Design 4 to complete hydrolysis reaction. After the solution cooled to room temperature, 1 mL of 1N HCl was added and the solution was diluted until 50 ml with mobile phase. The obtained solution was filtered through a 0.45 µm PTFE filter before HPLC injection.

One preferred embodiment of the bioabsorbable textiles showed a percentage of esterification of about 94.58% (Design 1), one other preferred embodiment of the bioabsorbable textiles showed a percentage of esterification of about 91.03% (Design 2), one other preferred embodiment of the bioabsorbable textiles showed a percentage of esterification of about 91.32% (Design 3), one other preferred embodiment of the bioabsorbable textiles showed a percentage of esterification of about 92.79% (Design 4), one other preferred embodiment of the bioabsorbable textiles showed a percentage of esterification of about 93.90% (HD1*).

Example 12: Determination of Free Benzyl Alcohol

Described herein the evaluation of free benzyl alcohol in four preferred embodiments of the leno-weave bioabsorbable textiles according to the present disclosure. The tested textiles of this example were those reported in Table 1.

The free benzyl alcohol was determined using HPLC 1260 Infinity Binary Pump equipped with an Infinity Poroshell 120 EC-C18 4.6×100 mm column. The mobile phase was a mixture of high purified water/acetonitrile 80/20, a flow rate of 1 ml/min, an injection volume of 20 µl, a column temperature of 30° C. and a detection wavelength of 254 nm were chosen.

A calibration curve with benzyl alcohol was prepared.

Around 100 mg of sample (n=1) were treated with 3.33 ml of acetonitrile to extract the free benzyl alcohol. The sample was filtered through a 0.45 µm PTFE filter. 0.5 ml of filtered solution was added to 0.5 ml of mobile phase before HPLC injection.

One preferred embodiment of the bioabsorbable textiles showed 0.023% (w/w) of free benzyl alcohol (Design 1), one other preferred embodiment of the bioabsorbable textiles 0.035% (w/w) of free benzyl alcohol (Design 2), one other preferred embodiment of the bioabsorbable textiles showed a peak lower than the limit of quantification (LOQ) (Design 3), one other preferred embodiment of the bioabsorbable textiles showed a peak lower than LOQ (Design 4).

Example 13: In Vitro Degradation Study

Described herein the evaluation of in vitro degradation in simulated physiological conditions of one preferred embodiment of the knitted bioabsorbable textile according to the present disclosure. The tested textiles of this example were those reported in Table 1.

Considering the composition of synovial fluid of the joints, the in vitro degradation study was performed in simulated synovial fluid (SSF). SSF will be prepared following Marques M R C et al., 2011, by solubilizing 3 g of HA in 1 L of PBS under magnetic stirring. The amount of synovial fluid present in a joint is about 0.5-4 ml within large joints such as the knee (Kraus, 2007). Therefore, in order to simulate clinical condition, HD1* was immersed in 3 ml of SSF (minimum volume to fully submerge the mesh) in 15 ml conical plastic tube and put in the oven at 37° C.

Six (N=6) specimens, 20×25 mm HD1* were tested for each time point: N=3 for mass loss and % of esterification tests and N=3 for mechanical properties.

Figure 10A:
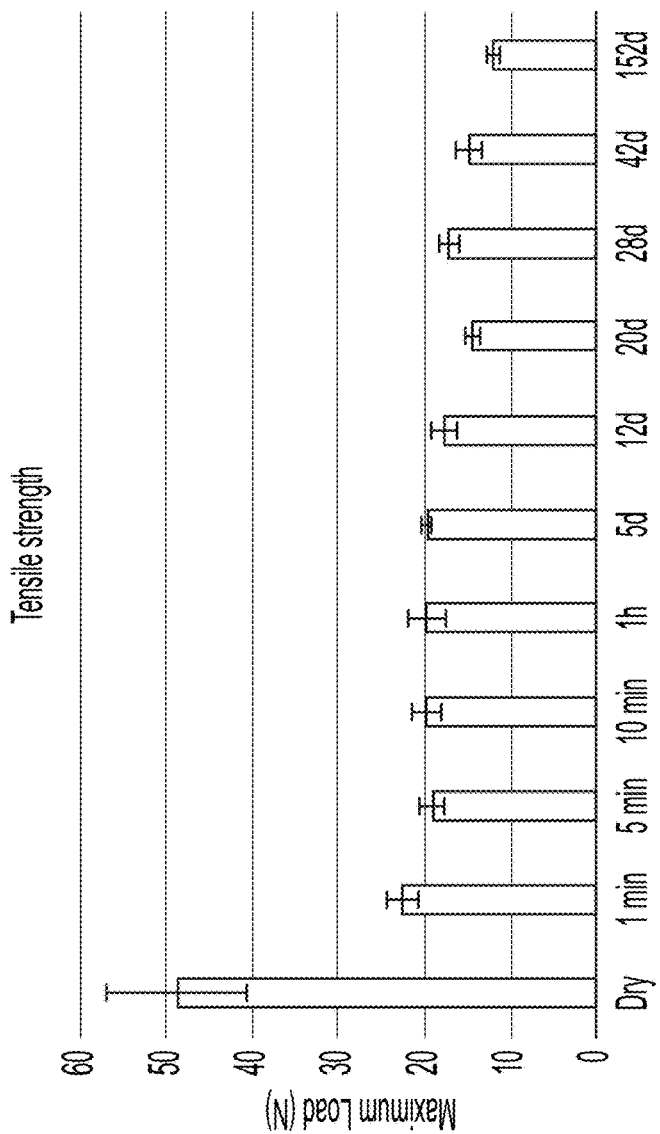
FIG. 10 shows the in vitro degradation results, FIG. 10A) Mechanical results.
FIG. 10B) % of mass loss during the time.
FIG. 10C) % of Hyaff11 esterification during the time as explained in Example 13.
Figure 10B:
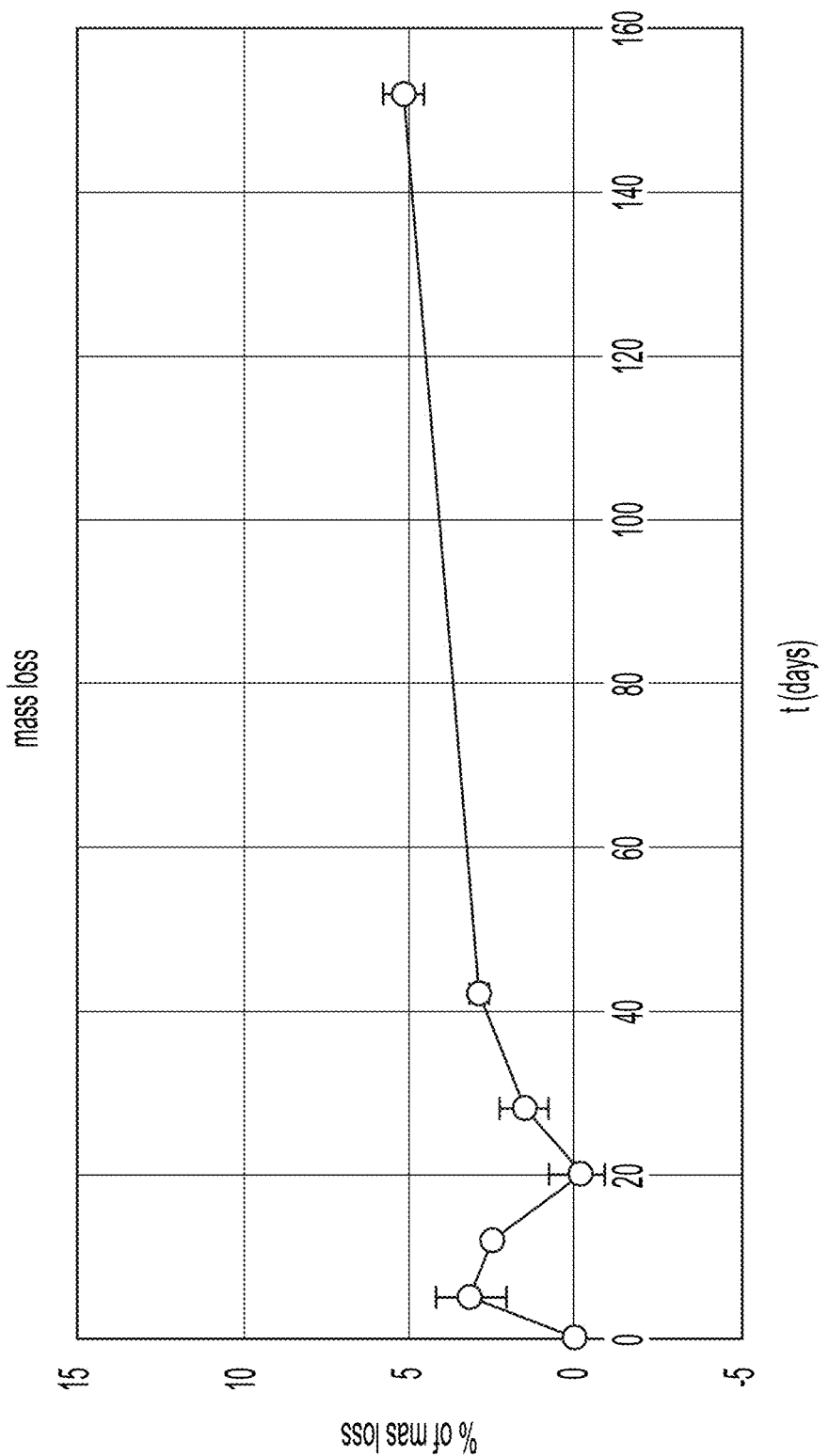
Figure 10C:
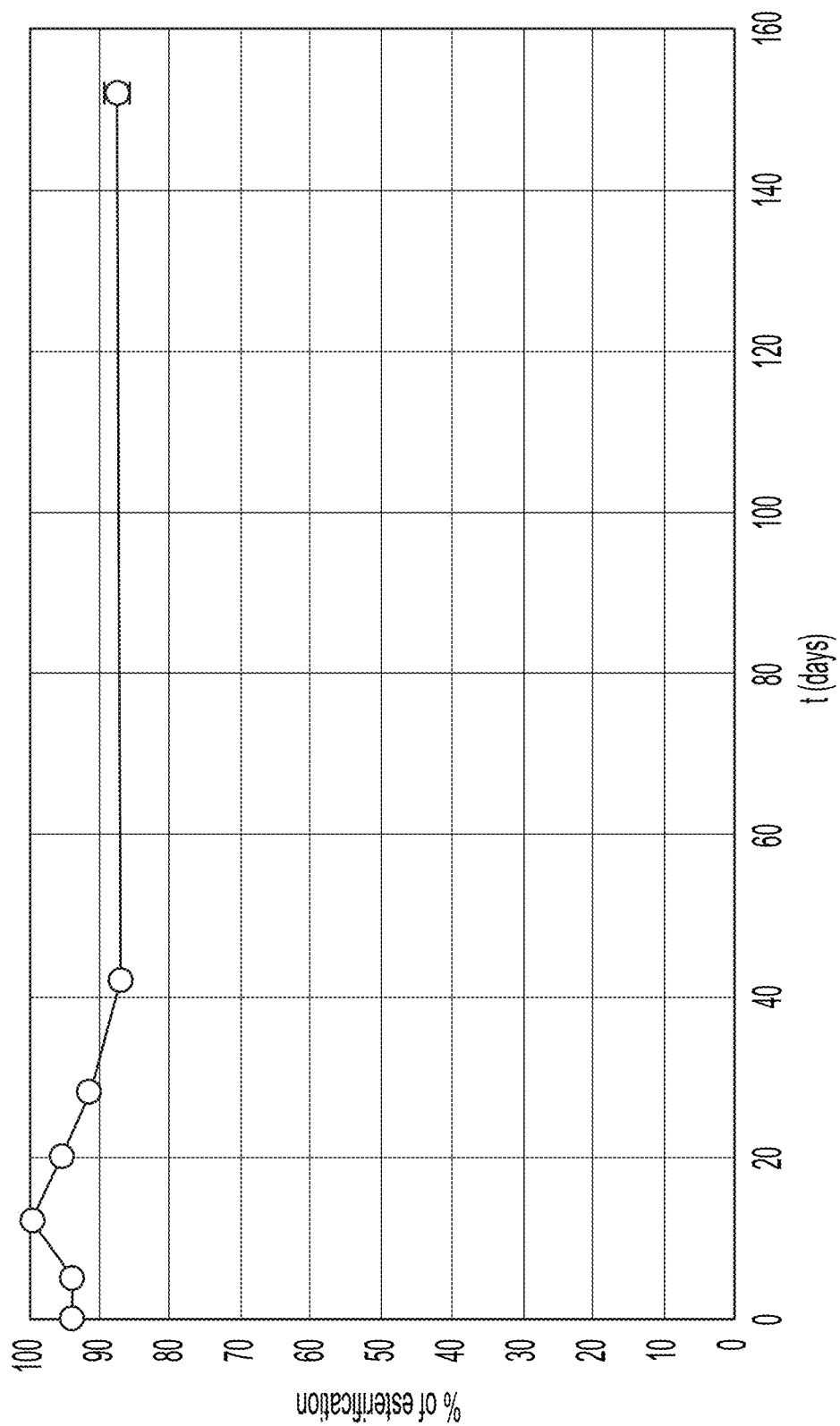

After 1 minute in SSF, HD1* lost about 50% of its mechanical strength, after 5 minutes until 5 days around 60% of its mechanical strength was lost, and after 152 days HD1* retained around 25% of initial maximum load (FIG. 10A). After 152 days, HD1* lost about 5% of its initial mass and showed a % of esterification of about 87% (FIG. 10B and FIG. 10C).

Example 14: In Vitro Cytotoxicity

Described herein is the assessment of in vitro cytotoxicity of some preferred embodiments of the bioabsorbable textiles (hereafter referred as "test samples"). The tested textiles of this example were those reported in Table 1.

The test was conducted by following the ISO 10993-5: 2009 with slight adaptations, using liquid extracts of the test samples. The samples were washed with isopropanol and dried before the test. Extraction method is particularly indicated for biodegradable and absorbable materials, for which not only leachable chemicals, but also degradation products must be tested for possible toxicity. The extraction of test samples was performed for 24±2 h at 37±1° C. using cell culture medium with serum as vehicle. The volume of extraction vehicle was calculated following what suggested in the ISO 10993-12:2012. The extraction vehicle not containing the test sample, retained in a vessel identical to the one used for the test samples, was incubated for 24±2 h at 37±1° C. and employed as Control. The Hyalonect extract was produced following the same conditions and used as an additional control. The cell line on which liquid extracts were tested was NIH 3T3 mouse fibroblasts, sub-cultured at least once before use. The extracts were incubated with cells for 24±2 h. Then the quantitative determination of cytotoxicity was done by MTS assay. The metabolic activity of cells put in contact with extracts was compared to that of the Control, which was assumed as 100% viability; then, cell viability (%) of each test condition was extrapolated thereby. Four preferred embodiments of the bioabsorbable textiles resulted in a relative cell viability of 83.19±6.72% (Design 1), 79.75±3.28% (Design 2), 98.44±3.60% (Design 3), 97.29±3.42% (Design 4), and 94.38±6.10% (LD2) respectively. The effect of the textiles on cells was statistically equivalent or even better than that of the Hyalonect, producing a relative cell viability of 83.65±8.15% compared to Control. Overall, since all embodiments passed the cell viability threshold of 70% of Control, the bioabsorbable textiles can be considered not cytotoxic.

Example 15: In Vitro Quantitative Assessment of Collagen Production

Figure 11:
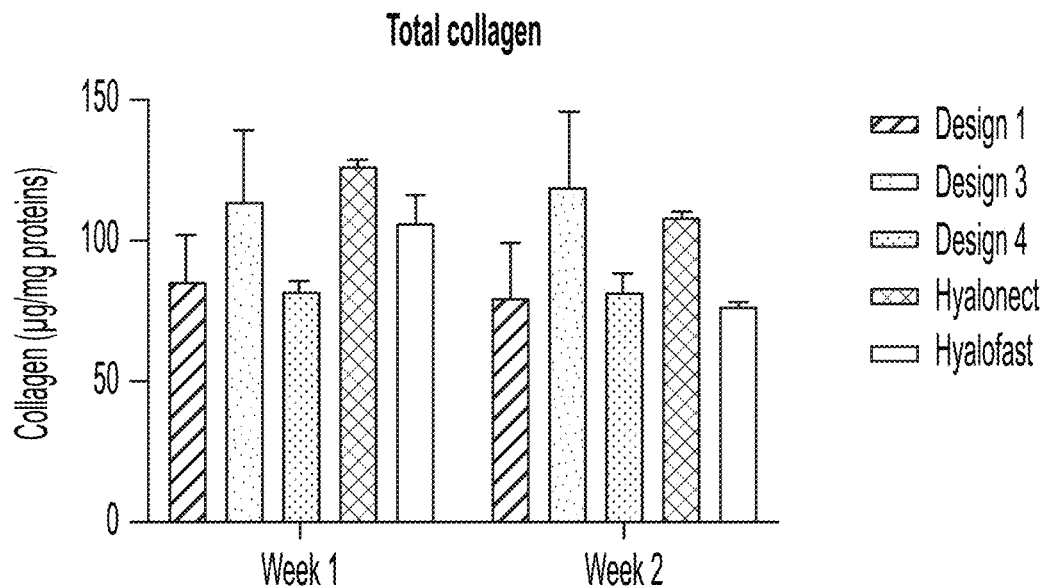
FIG. 11 shows the results of the in vitro quantitative assessment of collagen production of Example 15, specifically the quantity of total collagen after 1 and 2 weeks of cell culture. Error bars represent standard deviation.
Figure 12:
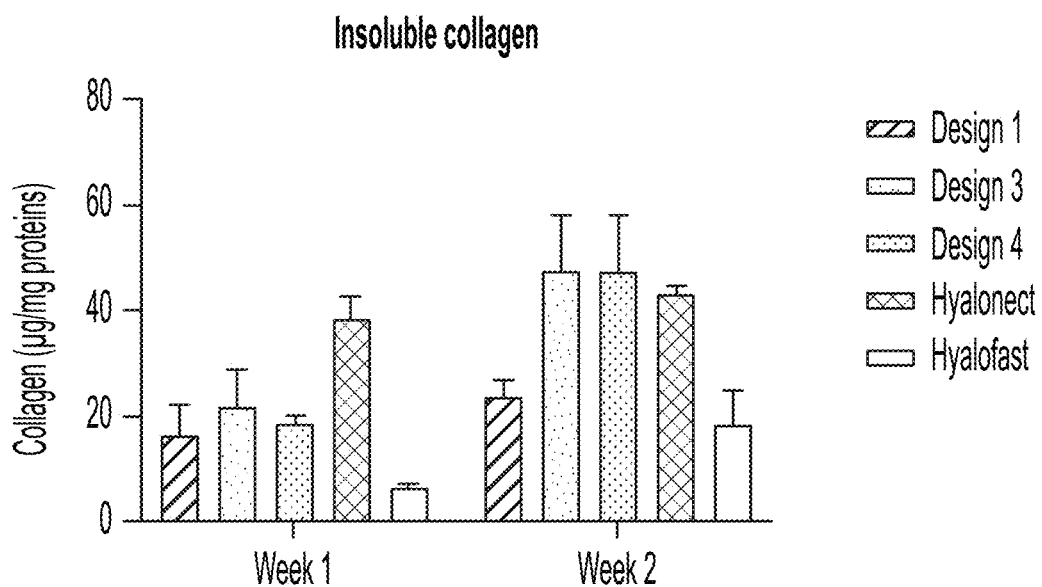
FIG. 12 shows the results of the in vitro quantitative assessment of collagen production of Example 15, specifically the quantity of insoluble, mature collagen after 1 and 2 weeks of cell culture. Error bars represent standard deviation.

Suitable scaffolds for cell culture were generated by cutting each textile sample with sterile scissors. The dimensions of the scaffolds were 6.8±0.2 mm×13 mm for Design 1, 7.5±0.3 mm×13 mm for Design 2, and 5.0±0.1 mm×15 mm for Design 3 and 4. HYALOFAST® of similar dimensions was used as control, proven to be a suitable cell scaffold and not to inhibit new collagen deposition. NIH 3T3 culture was performed with an initial cell number of 2 million seeded on each scaffold, in low adhesion 24-well plates. After overnight incubation in standard culture medium, cell-loaded textile samples were transferred to new wells and cultured in 1.5 mL of standard culture medium for 4 days to allow cell expansion; the culture medium was then substituted with the differentiation medium (DMEM High Glucose+2 mM L-Glutamine+1% PenStrep+1% HEPES+1% ITS, supplemented with 300 µg/mL of Ascorbic Acid 2-phosphate and 2 ng/mL of TGFβ1), in which cell-loaded textile samples were cultured for 1 week. The medium was changed twice a week and collagen production was measured at 7 and 14 days. Newly-formed soluble collagen and insoluble collagen fibers were quantified with dedicated kits, the S1000 Sircol Collagen Assay and the S2000 Sircol Insoluble Collagen Assay, respectively (Biocolor). Appropriate calibration curves with collagen standards, provided by the kit, were built at each assay run. Soluble collagen was quantified, according to the specific kit protocol, from the spent culture medium retrieved and stocked at −80° C. at each medium change. As far as concerned insoluble collagen determination at the established time points, the S2000 Sircol Insoluble Collagen Assay protocol required some adaptation for these textiles. The manufacturer's instructions recommended to start the protocol with tissue samples of 20-30 mg of wet weight, but the measured wet weight of entire scaffolds was 94.65±24.26 mg. Thus, depending on its wet weight, each textile sample was cut into three to five similar portions, which were treated as 3 different samples for S2000 Sircol Insoluble Collagen Assay. The insoluble collagen quantity per textile sample (experimental sample) was reconstructed by summing the measured collagen quantities of the three to five derived samples. Finally, insoluble and soluble collagen quantities for each experimental sample were summed to gain total collagen, whose value was normalized on the total amount of proteins in the same sample, assessed by Bradford method. Results indicated that a considerable amount of total collagen was present in all textile samples, with only some embodiments (Design 1 and Design 3) equaling the total amount of collagen produced on HYALOFAST® at day 7. However, at day 14, all embodiments were comparable or even better than HYALOFAST® in terms of total collagen production. Moreover, looking just at the mature, insoluble (cross-linked) collagen, the most relevant collagen fraction in a tendon healing context, all embodiments surprisingly displayed higher performances compared to HYALOFAST® at both timepoints, supporting the deposition of higher insoluble collagen quantities. This unexpected and exceptional finding has been attributed to the potential of the textile longitudinally-oriented fibers to support fast and mature collagen deposition. Data were summarized in FIGS. 11-12.

Example 16: Preliminary Evaluation of the Efficacy and Local Tissue Response in a Sheep Model Sheep were selected for this pilot study because of the similarities to humans in terms of healing rate and shoulder anatomy. Ovine models are well established and accepted in rotator cuff research (Coleman at al., 2003). Two animal studies were performed, one with leno-weave bioabsorbable textiles and one with knitted textiles.

Figure 13:
FIG. 13 shows the results of the preliminary evaluation of the efficacy and local tissue response in a sheep model, specifically an intraoperative picture of the bioabsorbable textile (Design 1) implanted in an ovine infraspinatus tendon model.

The study with leno-weave bioabsorbable textile of Table 1 has been conducted based on ISO 10993-6. In 8 sheep, the infraspinatus tendon of the right leg was surgically released by two third of its width and with a full-thickness lesion. Two modified Mason-Allen sutures (at a minimum) were preplaced in the tendon at transection using 2 Fiber Wire. The bone at the detached insertion was decorticated using a nitrogen powered 4 mm burr. A minimum of 3 holes were drilled into the proximal humerus (using a 2 mm bit). Sterile saline was used for irrigation during drilling. The ends of the Fiber Wire were tunneled through these holes. At this point, 4 animals were randomly assigned to the Repair-only group (Group 1) and the other 4 animals to the Augmentation group (Group 2). For animals assigned to Group 1, no further treatment of the repair site was conducted; the tendon repair was completed. For animals assigned to Group 2, the bioabsorbable textile (Design 1) was affixed to the repaired tendon and anchored appropriately to the humerus. Two modified Mason-Allen sutures (0 Fiber Wire) were preplaced through the augmentation device and the tendon. An additional hole (burr size 2 mm) was drilled into the proximal humerus and a cortical bone screw and spiked washer was used to affix the distal end of the augmentation device to the bone. The preplaced Mason-Allen sutures were tied to allow for appropriate tension of the augmentation device over the repaired tendon (FIG. 13). Recovery from the anesthesia took place in the animal housing. Each animal was placed in a suspension system prior to recovery from anesthesia. Each animal was placed in the suspension system so that the animal was slightly elevated above the ground or was able to toe touch but was unable to bear full body weight on any limb for 14 days post-op.

At 6 and 12 weeks (±3 days) post-surgery, two animals per each group, arbitrarily selected, were euthanized to evaluate healing of repair site, local tissue response and degradation of the textile. The tendons and repair site were macroscopically observed to determine if they were intact and whether obvious relative movements had occurred. Absorption and degradation of the textile was scored according to defined criteria; efficacy of healing was addressed using pathologist defined criteria. For microscopic evaluation, tendon and repair site, as well as right and left axillary lymph nodes were collected and adequately treated for sectioning and histological analysis. The tissue characteristics observed were neovascularization, fibrosis, fatty infiltrate and necrosis, while the monitored cell types included polymorphonuclear cells, lymphocytes, plasma cells, macrophages and giant cells. Tissue and cellular alterations were graded according to severity (0-4) based on the scoring scheme in Annex E of ISO 10993-6. Moreover, tissue sections from the regional draining lymph nodes were evaluated for textile particles.

All animals survived to scheduled necropsy. At necropsy, all repair sites were macroscopically normal. Microscopically, the local reaction to the bioabsorbable textile at both 6- and 12-weeks post-surgery was consisted of minimal to mild numbers of macrophages and multinucleated giant cells, minimal to mild neovascularization, severe fibrosis/ fibroplasia, and minimal fatty infiltrate. Inflammatory cells were almost exclusively found adjacent to suture and/or textile material. There was abundant extracellular textile material in all implant sites at 6 weeks post-surgery and significantly decreased until no extracellular textile material could be observed at 12 weeks post-surgery. Microscopic findings in the left and right axillary lymph nodes in test and control animals at either 6- or 12-weeks post-surgery were similar, and no adverse reactions were observed. There was no evidence of textile material within the microscopically examined axillary lymph node sections at either 6- or 12-weeks post-surgery.

Figure 14:
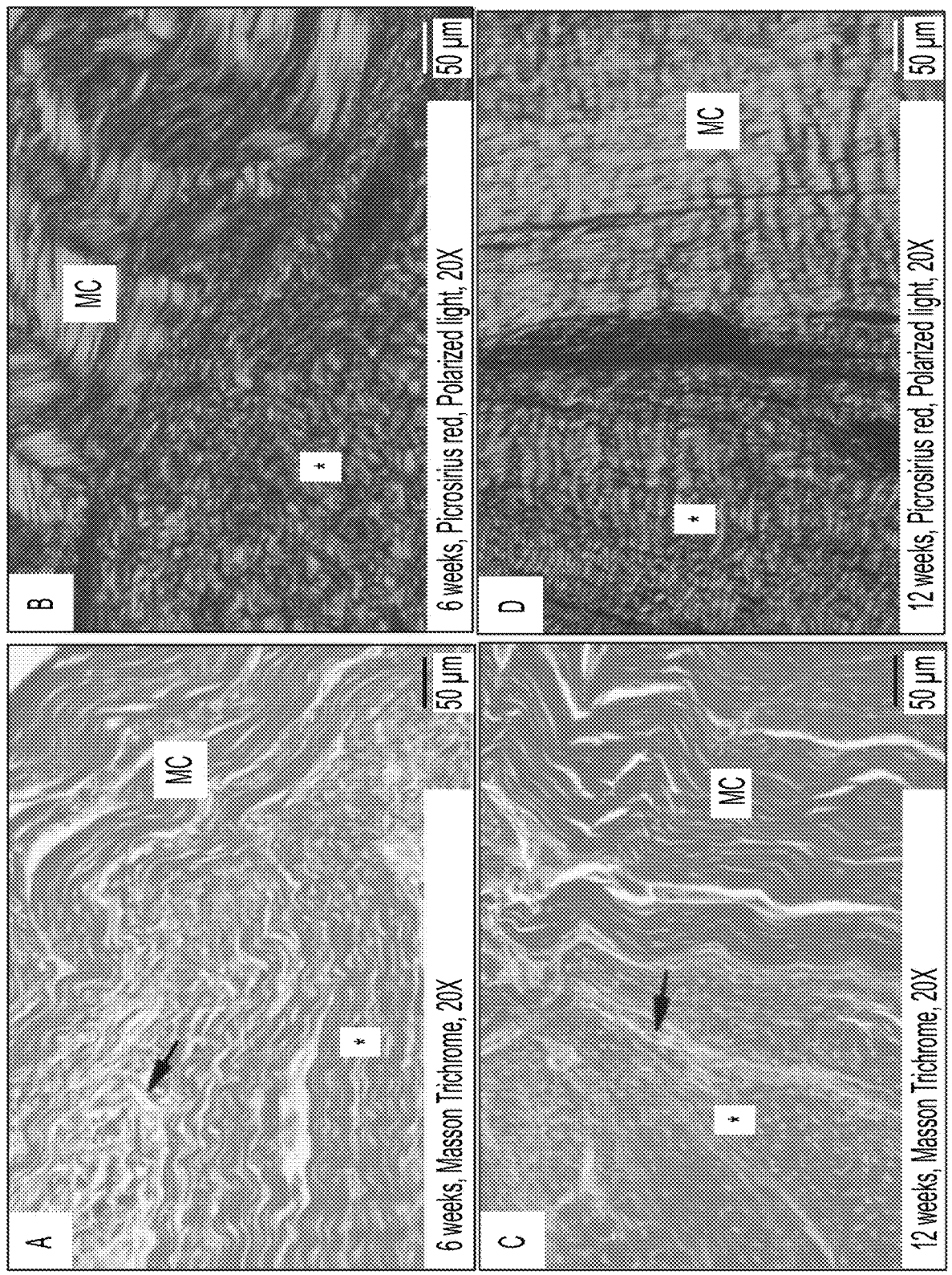
FIG. 14 shows the results of the preliminary evaluation of the efficacy and local tissue response in a sheep model, specifically histological pictures of Group 2 at 6 weeks (A. Masson Trichrome and B. Picrosirius red under polarized light) and at 12 weeks (C. Masson Trichrome and D. Picrosirius red under polarized light). 20× Magnification. Scale bar: 50 µm.

Cellular homing as well as newly-formed extracellular collagenous matrix could be observed in the textile-augmented animals (Group 2) already at 6 weeks (FIG. 14A-B) with an increasing trend visible at 12 weeks (FIG. 14C-D). The final phase of healing, when tissue remodeling takes place and immature collagen is replaced with mature collagen, was still underway and could only be appreciated at longer timepoints.

Figures 15A, 15B, 15C:
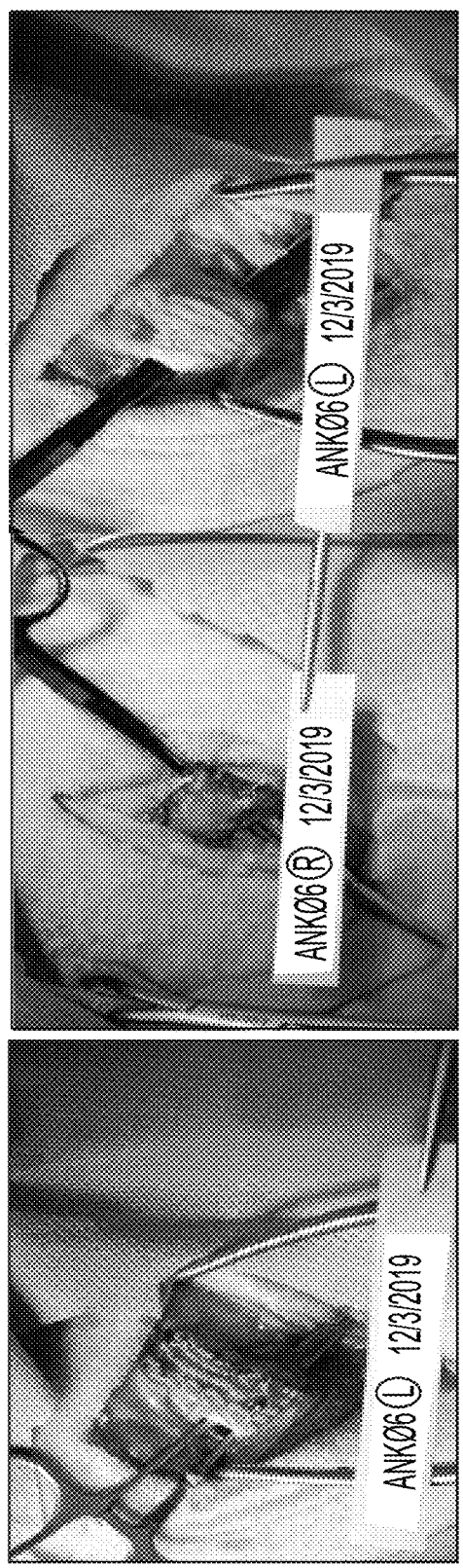
FIG. 15B) Regeneten implanted and FIG. 15C) no augmentation (Control) in an ovine infraspinatus tendon disruption model.

The study with knitted bioabsorbable textiles of Table 1 has been conducted using LD2 in double layer configuration (Treatment 1) and LD2 in double layer configuration with a non-woven pad (Treatment 2) based on HA benzyl ester between the two layers. Eight (8) animals were prepared for surgery and a bilateral combed fenestration (tendon disruption) of the infraspinatus tendons will be performed, the test articles described above were implanted in an overlay fashion on top of the disrupted tendon according to van Kampen et al, Muscles, Ligaments and Tendons Journal 2013. The fenestrations were made parallel to the infraspinatus tendon fibers. The tendon was not released from the humeral footprint. This "combing" procedure occurred only one time resulting in 4 fenestrations along the long axis of the tendon. Two pilot holes were drilled into the humerus along the distal edge of the infraspinatus tendon. Two ConMed CrossFT PEEK anchors loaded with Hi-Fi tape were deployed into the holes. The bioabsorbable textile was placed on top of the infraspinatus tendon and humeral footprint and sutured along the distal, lateral, medial and proximal edges using the Hi-Fi tape from each of the suture anchors. After the implantation, the animals were survived either until 6-weeks (+/−4 days) or 12-weeks (+/−4 days). Regeneten was used as a positive control group, and no augmentation was used as a negative control group (FIG. 15C).

Figure 16:
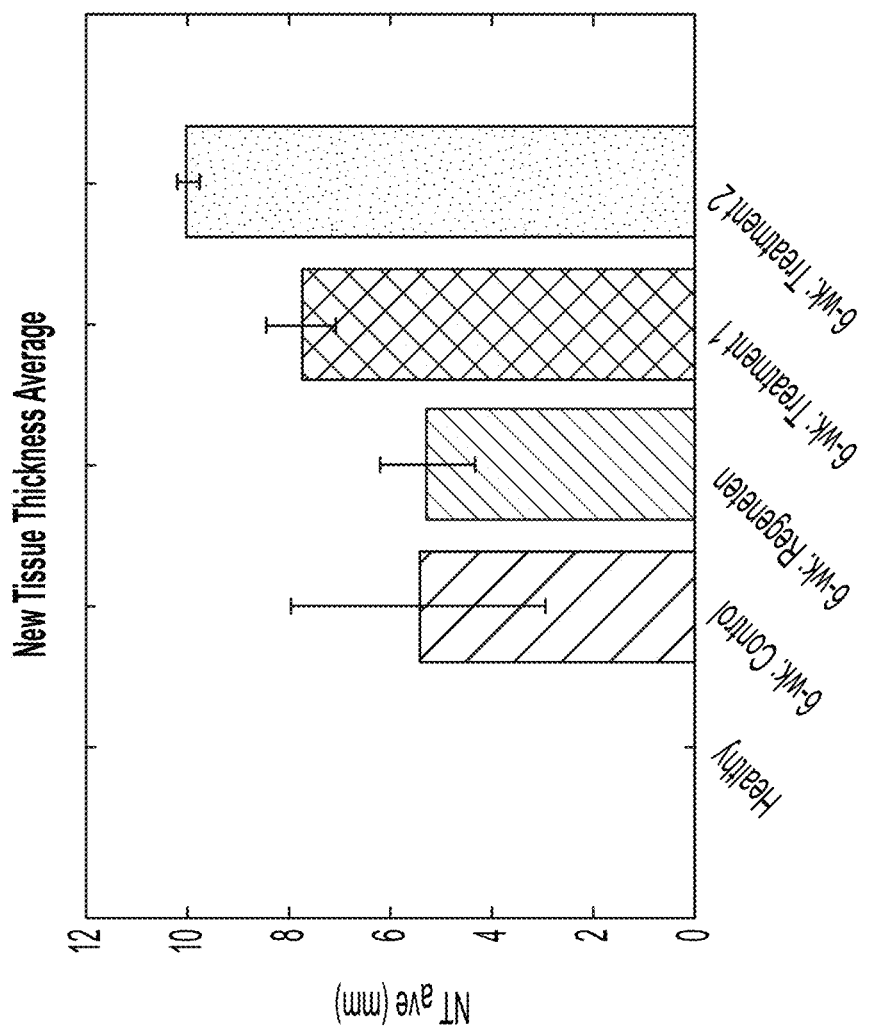
FIG. 16 shows the results of the preliminary evaluation of the efficacy and local tissue response in a sheep model, specifically the tendon thickness analysis at 6 weeks.
Figure 17B:
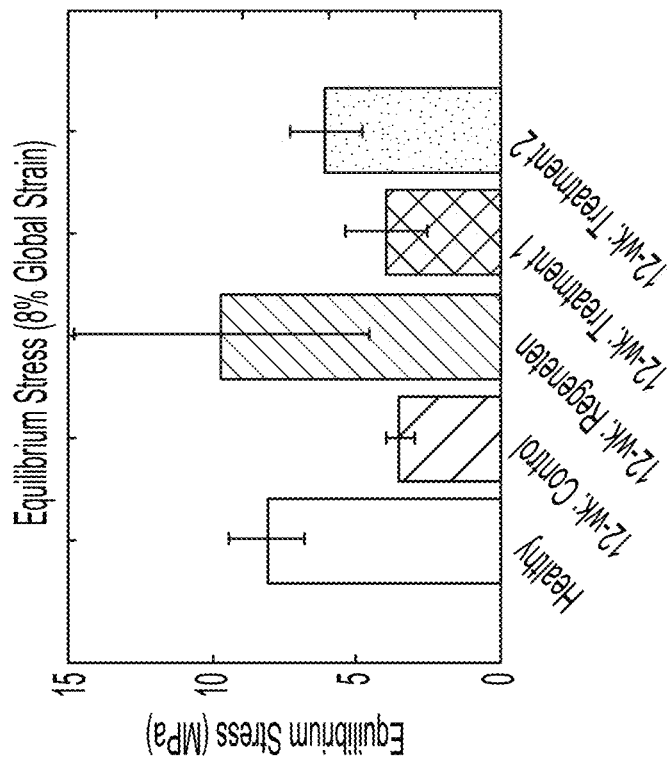
FIG. 17 shows the results of the preliminary evaluation of the efficacy and local tissue response in a sheep model, specifically the Peak Stress (8% Global Strain, FIG. 17A) and Equilibrium Stress (8% Global Strain, FIG. 17B) analysis at 12 weeks.
Figure 17A:
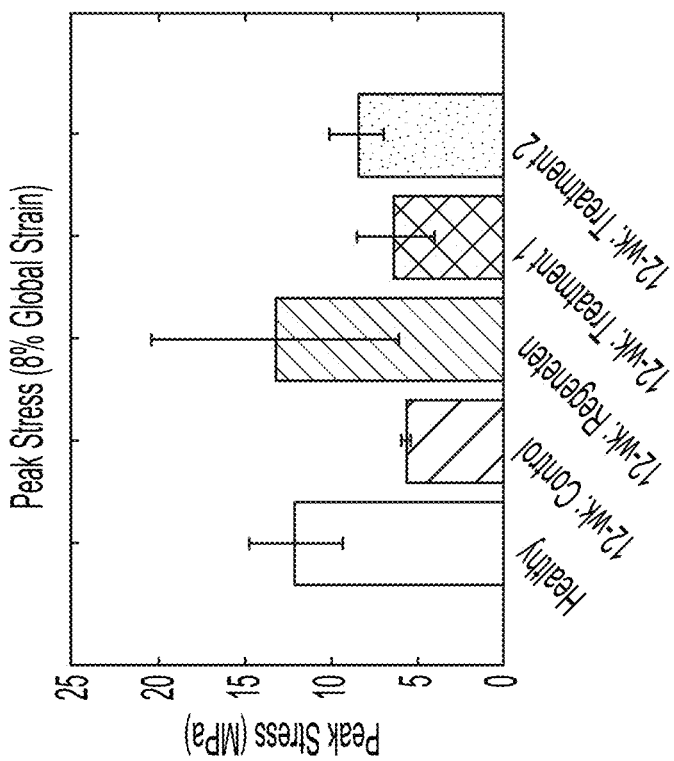
Figure 18A:
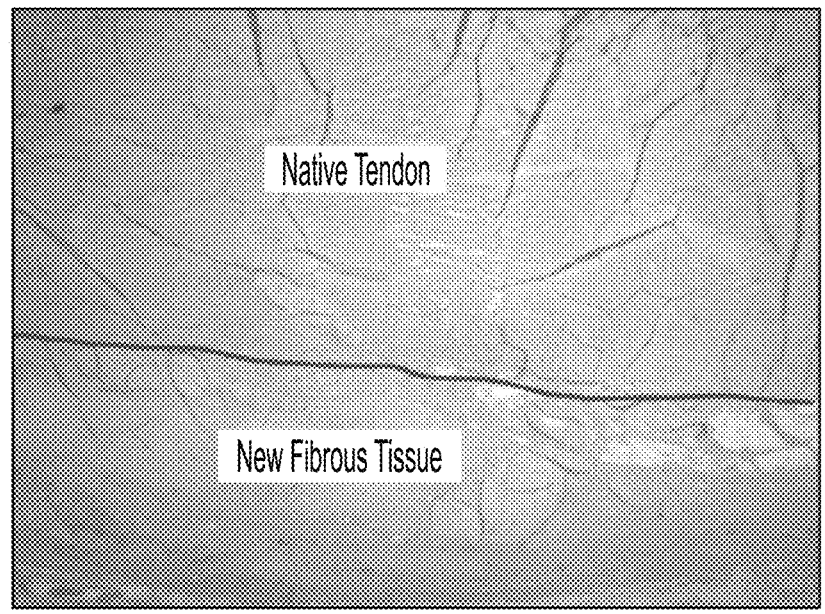
FIG. 18A shows the results of the preliminary evaluation of the efficacy and local tissue response in a sheep model, specifically the histological Overview after Regeneten in Ovine Tendon Disruption Model after 12 weeks.
Figure 18B:
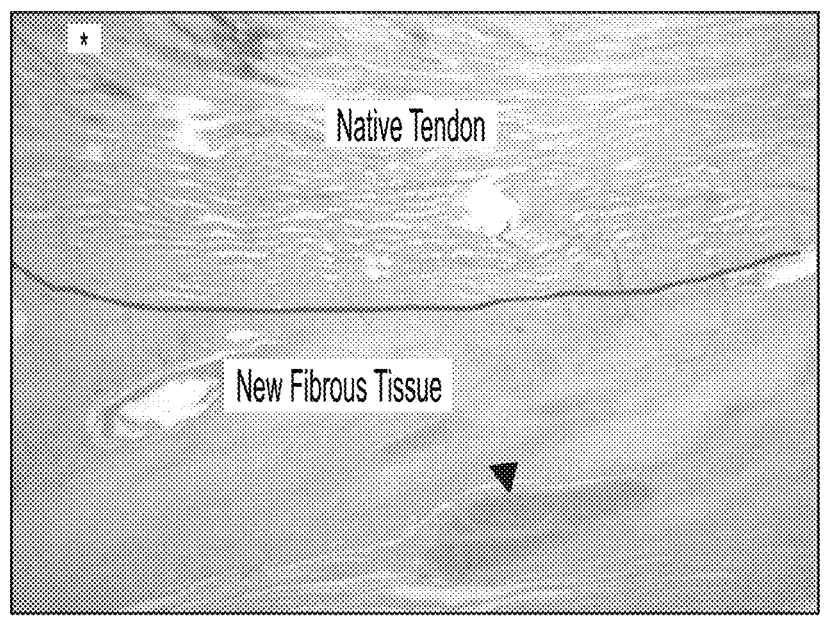
FIG. 18B shows the results of the preliminary evaluation of the efficacy and local tissue response in a sheep model, specifically the histological Overview after Treatment-1 in Ovine Tendon Disruption Model after 12 weeks.
Figure 18C:
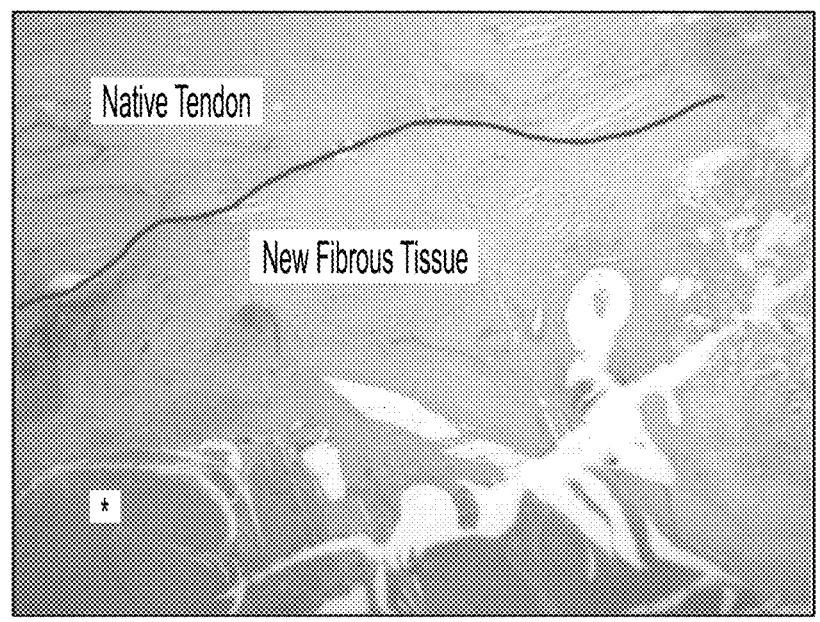
FIG. 18C shows the results of the preliminary evaluation of the efficacy and local tissue response in a sheep model, specifically the histological Overview after Treatment-2 in Ovine Tendon Disruption Model after 12 weeks.

Results of overlay model: All explanted samples exhibited new tissue growth at 6-weeks, while the knitted textile treated tendons (Treatment 1 and 2) exhibited significantly more new tissue thickness at 6-weeks as compared to the negative control and Regeneten (FIG. 16). At 12-weeks, knitted textile test articles (Treatment 1 and 2) exhibited improved Peak Stress (8% global strain) and Equilibrium Stress (8% global strain) as compared the control samples, and comparable values to Regeneten (FIG. 17A and FIG. 17B). Histologically, the knitted textile test articles (Treatment 1 and 2) and Regeneten samples elicited similar biological responses, and both displayed a mild trend towards increased neo-vascularization and decreased inflammation, as compared to control animals at 6 weeks. There was an overall increase in collagen fiber organization in the knitted textile treatments from the 6-week timepoint to the 12-week timepoint. By 12-weeks, the performance of the knitted textile test articles (Treatment 1 and 2) were similar to Regeneten characterized primarily by degree of collagen organization, cellularity and the presence of Sharpey fibers. (FIG. 18A, B, C).

Example 17: Multi-Layered Structure

Described herein is a method to incorporate differential mechanical and morphological properties into a single composite textile. In this exemplary embodiment, a 2.5 cm×2.5 cm sheet of High Density Single Bar (HD1) warp-knitted textile and a 2.5 cm×2.5 cm sheet of non-woven pad based on HA benzyl ester are bonded together to form a single composite multi-layered bioabsorbable textile. The HD1 textile is placed on a foil release layer, then dabbed with a lint-free laboratory wipe soaked with dimethyl sulfoxide (DMSO). The non-woven pad based on HA benzyl ester is then placed on top of the HD1 textile and covered with a second foil release layer. The entire multi-layered structure is then subjected to heat and pressure by placing in a FS-205 Impulse Sealer and activating with approximately 50 N of force for 5-10 seconds. The composite textiles are then removed and dried overnight in a vacuum oven to remove any residual DMSO.

REFERENCES

Aurora A, Gatica J E, den Bogert A J, McCarron J A, Derwin K A. An analytical model for rotator cuff repairs. Clin Biomech 2010; 25:751-758.

Aurora A, Mesiha M, Tan C D, Walker E, Sahoo S, Iannotti J P, McCarron J A, Derwin K A. Mechanical characterization and biocompatibility of a novel reinforced fascia patch for rotator cuff repair. Journal of Biomedical Materials Research A 2011; 99A: 221-230.

Barber F A, Herbert M A, Coons D A. Tendon Augmentation Grafts: Biomechanical Failure Loads and Failure Patterns. Arthroscopy: The Journal of Arthroscopic and Related Surgery 2006; 22:534-538

Bishop J, Klepps S, Lo I K, Bird J, Gladstone J N, Flatow E L. Cuff integrity after arthroscopic versus open rotator cuff repair: a prospective study. J Shoulder Elbow Surg 2006; 15:290-299.

Burkhart S S, Diaz Pagan L, Wirth M A, Ahanasiou K A. Cyclic loading of anchor-based rotator cuff repairs: Confirmation of the tension overload phenomenon and comparison of suture anchor fixation with transosseous fixation. Arthroscopy 1997; 13:720-724.

Caliari S R, Ramirez M A, Harley B. The development of collagen-GAG scaffold-membrane composites for tendon tissue engineering. Biomaterials 2011; 32(34): 8990-8998.

Chen J, Xu J, Wang A, Zheng M. Scaffolds for tendon and ligament repair: review of the efficacy of commercial products. Expert Rev Med Devices 2009; 6:61-73.

Coleman S H, Fealy S, Ehteshami J R, MacGillivray J D, Altchek D W, Warren R F, Turner A S. Chronic rotator cuff injury and repair model in sheep. J Bone Joint Surg Am. 2003 December; 85(12):2391-402.

Derwin K A, Codsi M J, Milks R A, Baker A R, McCarron J A, and Iannotti J P. Rotator cuff repair augmentation in a canine model with use of a woven poly-L-lactide device. Journal of Bone and Joint Surgery A 2009; 91:1159-1171.

Funakoshi T, Majima T, Iwasaki N, Suenaga N, Sawaguchi N, Shimode K, Minami A, Harada K, Nishimura S. Application of Tissue Engineering Techniques for Rotator Cuff Regeneration Using a Chitosan-Based Hyaluronan Hybrid Fiber Scaffold. The American Journal of Sports Medicine 2005; 33(8).

Galatz L M, Ball C M, Teefey S A, Middleton W D, Yamaguchi K. The outcome and repair integrity of completely arthroscopically repaired large and massive rotator cuff tears. J Bone Joint Surg Am 2004; 86-a:219-224.

Grier W K, Iyoha E M, Harley B. The influence of pore size and stiffness on tenocyte bioactivity and transcriptomic stability in collagen-GAG scaffolds. J Mech Behav Biomed Mater 2017; 65: 295-305.

Hughes R E, An K N. Force analysis of rotator cuff muscles. Clin Orthop Relat Res 1996; 330:75-83.

Kishore V, Bullock W, Sun X, Van Dyke W S, Akkus O. Tenogenic differentiation of human MSCs induced by the topography of electrochemically aligned collagen threads. Biomaterials 2012; 33(7):2137-2144.

Kraus V B, Stabler T V, Kong S Y, Varju G, McDaniel G. Measurement of synovial fluid volume using urea. Osteoarthritis Cartilage. 2007 October; 15(10):1217-20.

Lehman C, Cuomo F, Kummer F J, Zuckerman J D. The incidence of full thickness rotator cuff tears in a large cadaveric population. Bull Hosp Jt Dis 1995; 54:30-31.

Longo U G, Lamberti A, Maffulli N, Denaro V. Tendon augmentation grafts: a systematic review. Br Med Bull 2010; 94:165.

Marques M R C, Loebenberg R, Almukainzi M. Simulated Biological Fluids with Possible Application in Dissolution Testing. Dissolution Technologies 2011, doi.org/10.14227/DT180311P15.

Minagawa H, Yamamoto N, Abe H, Fukuda M, Seki N, Kikuchi K, Kijima H, Itoi E. Prevalence of symptomatic and asymptomatic rotator cuff tears in the general population: From mass-screening in one village. J Orthop. 2013; 10(1):8-12.

Moffat K L, Kwei A S, Spalazzi J P, Doty S B, Levine W N, Lu H H. Novel nanofiber-based scaffold for rotator cuff repair and augmentation. Tissue Eng Part A 2009; 15(1): 115-126.

Ratcliffe A, Butler D L, Dyment N A, Cagle P J, Jr., Proctor C S, Ratcliffe S S, and Flatow, E. L. Scaffolds for tendon and ligament repair and regeneration. Ann Biomed Eng 2015; 43: 819.

Smith R D J, Carr A, Dakin S, Snelling S, Yapp C, Hakimi O. The response of tenocytes to commercial scaffolds used for rotator cuff repair. Eur Cell Mater 2016; 30:107.

Smith R D J, Zargar N, Brown C P, et al. Characterizing the macro and micro mechanical properties of scaffolds for rotator cuff repair. J Shoulder Elbow Surg. 2017; 26:2038-46.

Thangarajah T, Pendegrass C J, Shahbazi S, Lambert S, Alexander S, Blunn G W. Augmentation of rotator cuff repair with soft tissue scaffolds. The Orthopaedic Journal of Sports Medicine 2015; 3(6).

Tashjian, R Z. Epidemiology, natural history, and indications for treatment of rotator cuff tears. Clin Sports Med 2012; 31(4):589-604.

Tong W Y, Shen W, Yeung C W, Zhao Y, Cheng S H, Chu P K, Chan D, Chan G C, Cheung K M, Yeung K W et al. Functional replication of the tendon tissue microenvironment by a bioimprinted substrate and the support of tenocytic differentiation of mesenchymal stem cells. Biomaterials 2012; 33(31):7686-98.

Van Kampen C, Arnoczky S, Parks P, et al. Tissue-engineered augmentation of a rotator cuff tendon using a reconstituted collagen scaffold: a histological evaluation in sheep. Muscles Ligaments Tendons J. 2013; 3(3):229-235.

Yamamoto A, Takagishi K, Osawa T, Yanagawa T, Nakajima D, Shitara H, Kobayashi T. Prevalence and risk factors of a rotator cuff tear in the general population. J Shoulder Elbow Surg 2010; 19:116-120.

Younesi M, Islam A, Kishore V, Anderson J M, Akkus O. Tenogenic Induction of Human MSCs by Anisotropically Aligned Collagen Biotextiles. Adv Funct Mater. 2014; 24(36): 5762-5770.

Zhang X, Bogdanowicz D, Erisken C, Lee N M, Lu H H. Biomimetic Scaffold Design for Functional and Integrative Tendon Repair. J Shoulder Elbow Surg 2012; 21(2): 266-277.

The invention claimed is:

1. A bioabsorbable textile for joint function restoration comprising polymeric yarns,
    wherein at least one of said polymeric yarns comprises a hyaluronic acid derivative, and
    the at least polymeric yarn having:
        linear mass density from 30 tex to about 100 tex;
        a breaking strength in the range from about 1 N to about 100 N; and
        an extension at break from about 1% to about 30% and
    wherein the bioabsorbable textile is a knitted structure or a leno-wave structure.

2. The bioabsorbable textile according to claim 1, wherein said hyaluronic acid derivative is an ester.

3. The bioabsorbable textile according to claim 2, wherein said hyaluronic acid derivative is a benzyl ester.

4. The bioabsorbable textile according to claim 3, wherein the esterification degree of said hyaluronic acid derivative ranges between 80% to 100%.

5. The bioabsorbable textile according to claim 1, wherein said bioabsorbable textile is coated with an osteo-inductive and/or osteo-conductive material selected from the group consisting of hydroxyapatite, calcium phosphates, bone cements, demineralized bone matrix, titanium, magnesium, strontium, bioglasses, other resorbable glasses, and a combination thereof.

6. The bioabsorbable textile according to claim 1, wherein the bioabsorbable textile is added to a biological component selected from the group consisting of bone marrow aspirate, bone marrow aspirate concentrate, mesenchymal stem cells, bone marrow stem cells, adipose-derived stem cells, amniotic cells, micronized amniotic membrane, partially- or fully-digested tissue biopsies, aspirated adipose tissue, platelet rich plasma, autologous conditioned plasma, growth factors, and a combination thereof.

7. The bioabsorbable textile according to claim 1, wherein the bioabsorbable textile is characterized by a volumetric and by a thickness swelling ratio in the range from about 0.1% to about 150%.

* * * * *